US006339960B1

United States Patent
Costley et al.

(10) Patent No.: US 6,339,960 B1
(45) Date of Patent: Jan. 22, 2002

(54) NON-INTRUSIVE PRESSURE AND LEVEL SENSOR FOR SEALED CONTAINERS

(75) Inventors: R. Daniel Costley, Oxford; Mark Henderson, Long Beach, both of MS (US)

(73) Assignee: Mississippi State University, Missisppi, MS (US)

( * ) Notice: Subject to any disclaimer, the term of this patent is extended or adjusted under 35 U.S.C. 154(b) by 0 days.

(21) Appl. No.: 09/698,227

(22) Filed: Oct. 30, 2000

(51) Int. Cl.$^7$ ................................................ G01H 3/24
(52) U.S. Cl. ............................... 73/579; 73/52; 73/702
(58) Field of Search ......................... 73/579, 574, 570, 73/599, 602, 12.01, 52, 290 V, 702, 54.06

(56) References Cited

U.S. PATENT DOCUMENTS

| | | |
|---|---|---|
| 3,926,036 A | 12/1975 | Bower |
| 4,009,616 A | 3/1977 | Wonn |
| 4,187,718 A | 2/1980 | Shibasaki |
| 4,399,514 A * | 8/1983 | Hamasaki et al. .............. 73/52 |
| 4,406,157 A * | 9/1983 | Miyahara et al. .............. 73/52 |
| 4,409,029 A | 10/1983 | Larker et al. |
| 4,577,487 A | 3/1986 | Dooley |
| 4,852,392 A * | 8/1989 | Evans ......................... 73/41.2 |
| 4,869,097 A * | 9/1989 | Tittmann et al. ............... 73/52 |
| 5,062,296 A | 11/1991 | Migliori |
| 5,353,631 A * | 10/1994 | Woringer et al. .............. 73/52 |
| 5,540,096 A | 7/1996 | Woodcock et al. |
| 5,585,567 A | 12/1996 | Van Manen |
| 5,641,905 A | 6/1997 | Schwarz et al. |
| 5,708,190 A | 1/1998 | Seefeldt et al. |
| 5,869,747 A * | 2/1999 | Hulsman ....................... 73/52 |
| 6,026,686 A * | 2/2000 | Hattori et al. ................. 73/579 |

OTHER PUBLICATIONS

Thinnes, G.L., et al., "Resonance Analysis To Determine Pressurization of 55 Gallon Waste Containers", Idaho National Engineering Laboratory (U.S. Department of Energy), INEL–95/0635, published Dec. 1995.
Morse, P.M., "Vibration and Sound", Massachusetts Institute of Technology (American Institute of Physics), Chapter 5, § 19 and §21, published 1983.
Sinha, D.N., et al., "Noninvasive Drum Pressure Measurements Using Acoustic Resonance Spetroscopy", Los Alamos National Laboratory (Results of Sep. 19–20 1995 Study), published Oct. 24, 1995.
Costley, R. D., et al., "Acoustic Detection of Pressure in Sealed Drums", J. Acoustical Society of America, (2pEA4), vol. 106, No. 4, Pt. 2, pp. 2166–2167, Oct. 1999.
Reismann, H., "Elastic Plates Theory and Application", John Wiley & Sons, NY, Chapters 6 and 7, published 1988.
H. Patel et al., "Drum Pressure Monitor", Review of Progress in Quantitative Nondestructive Evaluation, vol. 18, pp. 2087–2093, 1999.
P. K. Raju, "Engineering Acoustics, Physical Acoustics and Structural Acoustics and Vibration: Acoustic Nondestructive Evaluation: New Directions and Techniques, Part II", J. Acoust. Soc. Am., vol. 106, No. 4, Pt. 2, pp, 2166–2167, Oct. 1999.
H. Patel, "The Mode Shapes and Natural Frequencies of Various Types of Storage Drums Under Different Pressures", Mississippi State University, pp. 1–54, Aug. 1998.

\* cited by examiner

*Primary Examiner*—Hezron Williams
*Assistant Examiner*—Jacques Saint-Surin

(57) ABSTRACT

A method and apparatus for determining the internal pressure of a sealed container are disclosed. The method involves: exciting a lid of the container so as to create at least two modes of vibration having separate frequencies, wherein said frequencies are fundamental, $f_1$, and a second frequency, preferably the second axisymmetric mode, $f_2$; detecting the vibration resulting from said exciting to determine $f_1$, and $f_2$; using $f_2$, which is indicative of internal pressure, to calculate a first value for internal pressure using a first mathematical model that is calibrated to the lid on the sealed container; using $f_1$, which is indicative of volume of contents, to calculate the volume of contents in the sealed container using a second mathematical model that is calibrated to the lid on the sealed container, wherein a natural frequency of said lid is a function of said internal pressure and said volume of contents; and compensating for said volume of contents to determine a second value for internal pressure, wherein said second value for internal pressure is more reliable than said first value for internal pressure. The apparatus for determining the internal pressure of a sealed container of the invention includes: means for exciting a lid of the container so as to create at least two modes of vibration having separate frequencies, wherein said frequencies are fundamental, $f_1$, and a second frequency, preferably the second axisymmetric mode, $f_2$; detecting means for detecting vibration resulting from the exciting of said container to determine $f_1$, and $f_2$; calculating means for calculating a first value for internal pressure of said container using $f_2$; calculating means for calculating the volume of contents of said container using $f_1$; wherein a natural frequency of said lid is a function of said internal pressure and said volume of contents; and calculating means for compensating for said volume of contents to determine a second value for internal pressure, wherein said second value for internal pressure is more reliable than said first value for internal pressure.

6 Claims, 26 Drawing Sheets

55 gallon Tight Head Drum 55 gallon Open Head Drum

Lid with stiffening rings

Clamp ring and bolt

DATA FROM A POPULATION OF 55-GALLON, TIGHT HEAD DRUMS.

THE SQUARES ARE THE AVERAGES OF THE FREQUENCIES AT EACH PRESSURE FROM FIG.6A. THE STRAIGHT LINE IS A LINEAR REGRESSION THROUGH THESE POINTS. THE ERROR BARS ARE ± TWO STANDARD DEVIATIONS CALCULATED FROM THE AVERAGES.

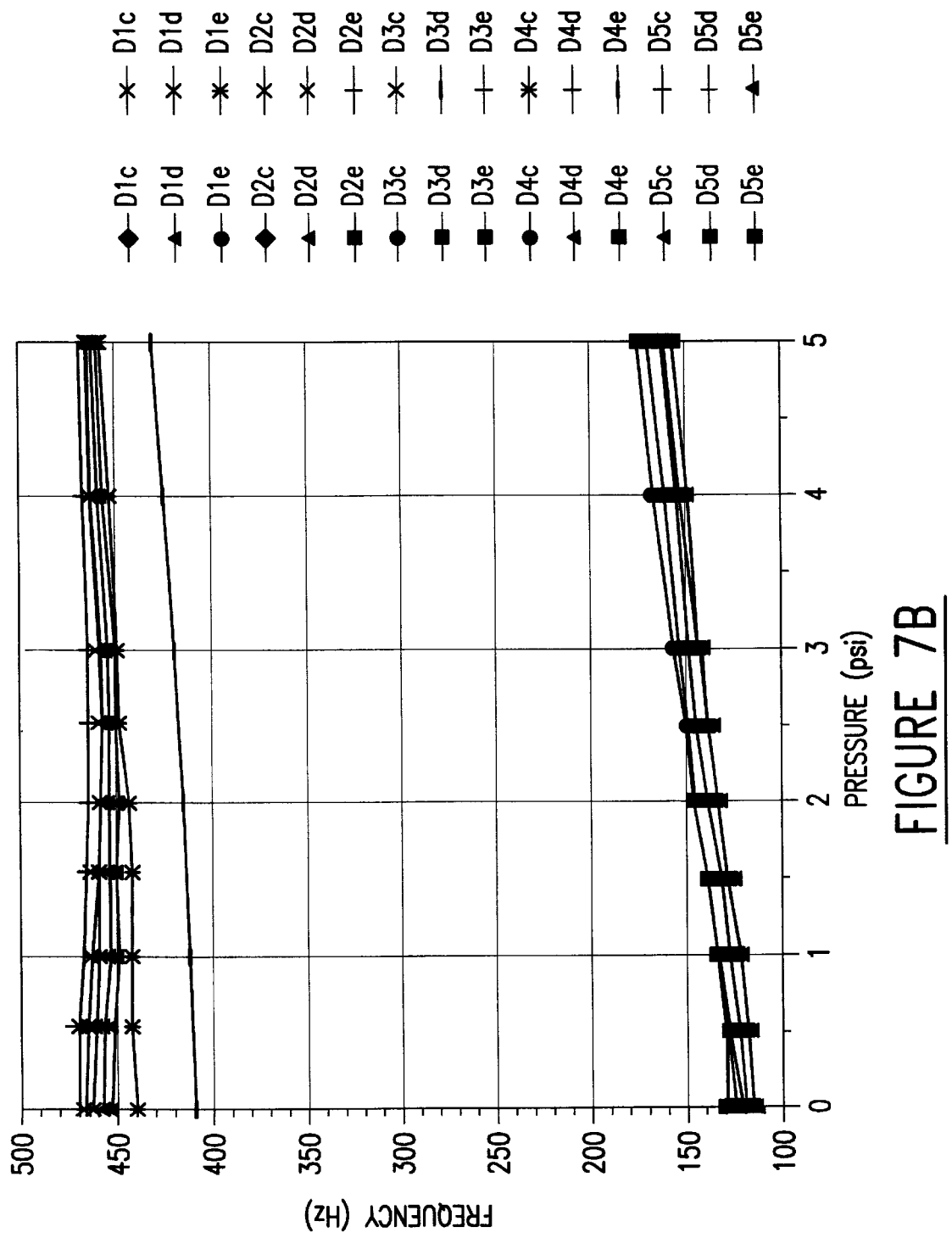

U.S. 6,339,960 B1

NON-INTRUSIVE PRESSURE AND LEVEL SENSOR FOR SEALED CONTAINERS

BACKGROUND OF THE INVENTION

1. Field of the Invention

The present invention relates to a method and apparatus for determining the internal pressure of a sealed container. The method and apparatus take into consideration variables that effect such determination, and in particular, the level of contents in the sealed container.

2. Background of the Prior Art

At many waste sites, transuranic (TRU), low-level, and mixed wastes are stored in 55-gallon drums. Many of these drums contain hazardous, organic waste as well. Radiolysis or other physical or chemical processes may result in gaseous emissions inside the drums. When this happens, the pressure within the drums increases, sometimes to unacceptable levels. In the most drastic cases, the emissions inflame or explode (e.g., due to hydrogen produced from radiolysis). Currently, regulatory procedures require that each drum be individually opened and inspected for the presence of hazardous organic waste. This procedure is dangerous for workers when drastic conditions such as described above exist. A non-intrusive technique that detects an increase in pressure over ambient would alert workers of potential danger while maintaining worker safety. Such a technique would also allow rapid segregation of suspect drums, thus providing more rapid treatment of safe drums.

There are a number of documented incidences in which drums have burst, or ruptured, and spilled their contents. In some cases workers have been injured. There thus exists a need to address the safety concerns associated with the handling of sealed drums of hazardous waste.

U.S. Pat. No. 4,009,616 discloses an acoustic method for measuring gas pressure in a hermetically sealed container. An acoustic signal is transmitted into and through the walls of the container along a path through a gas medium. The transmitted signal is received after it has traveled a given path through the gas medium and converted to a corresponding electrical output which is calibrated as a direct measure of the pressure of the gas.

U.S. Pat. No. 4,187,718 discloses a method and apparatus for determining the internal pressure of a sealed container by converting a sound wave excited at the wall of the container to a detectable electrical signal.

U.S. Pat. No. 5,585,567 discloses a method and apparatus for determining the internal pressure of a sealed container, which involve striking the wall of the container in a controlled manner so as to excite at least two modes of vibration having separate frequencies $f_1$ and $f_2$; and detecting a vibration resulting from the striking of the wall of the container.

Thinnes, G. L., et al. (1995) discloses resonance analysis techniques to detect subtle changes in a storage container lid's vibration characteristics caused by changes in internal pressure.

Patel et al. (1999) discloses a method for determining the internal pressure of a drum by determining a natural frequency of the drum lid. The method involves tapping the drum lid, recording the audible sound with a microphone, and converting the time-domain signal to a frequency spectrum using a Fast Fourier Transform.

The present inventors have determined that frequency measurements of a drum's lid can be used to accurately determine its internal pressure and that the frequency measurements are a function of a number of variables, including not only the internal pressure of the drum, but also the level of contents within the drum. None of the methods and apparatus described above take these variables into consideration when determining the safety of a sealed container.

SUMMARY OF THE INVENTION

The present invention is a simple, non-intrusive method and apparatus to more accurately determine the internal pressure of a sealed container (or storage drum).

The method for determining the internal pressure of a sealed container of the invention involves:

exciting a lid of the container so as to create at least two modes of vibration having separate frequencies, wherein said frequencies are fundamental, $f_1$, and a second frequency, $f_2$, preferably the second axisymmetric mode;

detecting the vibration resulting from said exciting to determine $f_1$ and $f_2$;

using $f_2$, which is indicative of internal pressure, to calculate a first value for internal pressure using a first mathematical model that is calibrated to the lid on the sealed container;

using $f_1$, which is indicative of volume of contents, to calculate the volume of contents in the sealed container using a second mathematical model that is calibrated to the lid on the sealed container, wherein a natural frequency of said lid is a function of said internal pressure and said volume of contents; and compensating for said volume of contents to determine a second value for internal pressure, wherein said second value for internal pressure is more reliable than said first value for internal pressure.

The apparatus for determining the internal pressure of a sealed container of the invention includes:

means for exciting a lid of the container so as to create at least two modes of vibration having separate frequencies, wherein said frequencies are fundamental, $f_1$, and a second frequency, $f_2$, preferably the second axisymmetric mode;

detecting means for detecting vibration resulting from the exciting of said container to determine $f_1$ and $f_2$;

calculating means for calculating a first value for internal pressure of said container using $f_2$;

calculating means for calculating a volume of contents of said container using $f_1$;

wherein a natural frequency of said lid is a function of said internal pressure and said volume of contents; and calculating means for compensating for said volume of contents to determine a second value for internal pressure, wherein said second value for internal pressure is more reliable than said first value for internal pressure.

The apparatus of the invention may be a laboratory instrument or a simple handheld instrument that works in real-time.

The present invention is illustrated below in greater detail with reference to non-limiting examples and accompanying drawings. It should be understood, however, that the present invention is not to be construed as being limited thereto.

BRIEF DESCRIPTION OF THE DRAWINGS

FIG. 7B is a graph showing the resonances of the fundamental and the second axisymmetric modes for the group of drum lids with the higher fundamental frequency from FIG. 6A.

DETAILED DESCRIPTION OF THE INVENTION

Figure 1A:
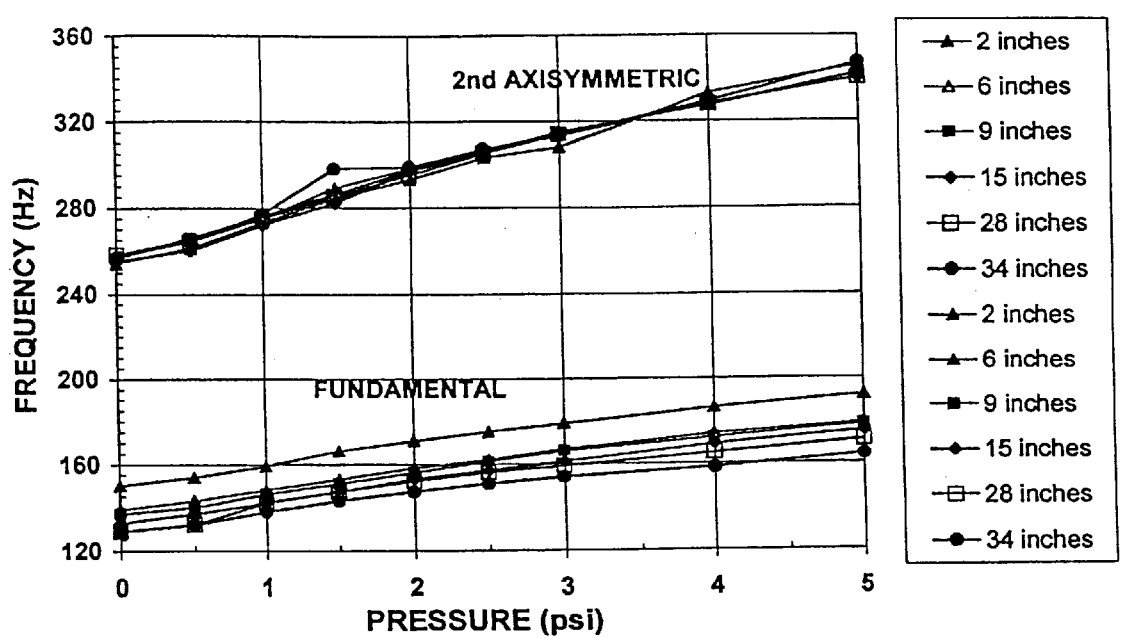
FIGS. 1A to 1C show how the frequency of the fundamental and second axisymmetric modes vary with pressure for different levels of contents.

All patents, patent applications and literature that may be cited in this disclosure are incorporated herein by reference in their entirety. In the case of inconsistencies, the present disclosure will prevail.

Metal storage drums come in a variety of sizes and configurations. Sizes range from about 10 gallons to about 110 gallons. The lids on tight-head drums are permanently fastened to the drum body, while the lids on open-head drums are removable. The tight-head drums have a bung hole in the lid. This is a hole approximately 3 inches in diameter through which the contents of the drum can be poured. A plug, or bung, screws into the bung hole to seal the drum.

The lid on 55-gallon, open-head drums can be removed from the drum body. The lid typically has a gasket around its outer edge which provides a seal between the drum and the lid. The lid is secured to the drum with a circular clamp ring and bolt. The circular clamp ring is torqued up to about 40 ft-lbs. The seal is designed to withstand an internal pressure of about 20 psig. The lid is clamped to the drum with an annular ring, which fits around the circumference of the drum. The lid (1b) may contain a bung hole (not shown).

Drums are made by several different manufacturers. They are commonly made from either 16 or 18 gauge steel, although drums made from other materials and with other gauges are available. Typically, the lid is stamped to form a slightly convex, or dome, shape. In addition to having a dome shape, a circumferential stiffening ring may be formed in the lid by the stamping operation.

Drums are used to store many different types of materials and objects, both liquid and solid. These may include contaminated soil, sludge, oil, chemicals, etc. Drums, especially open-bead drums, typically stand upright and are filled so that several inches of head-space remain between the contents and the drum lid (see FIG. 5E). In this commonly found configuration, none of the drum's contents are in contact with the lid. The present inventors have discovered that in addition to internal pressure, the volume of contents in the drum influences the vibration of the drum lid when the volume of contents in the drum is more than 80%. The present invention is thus a method and apparatus capable of taking the volume of contents into consideration when determining the internal pressure and thus the safety of a sealed container.

The present inventors studied the influence of several factors, both by Finite Element Modeling (FEM) and experimentally. In addition to pressure and fill level, the effects of gauge thickness, and stiffening ring on drum lid response were determined.

FEM is a computerized method used to solve engineering problems related to complex systems. A FEM is generated by reducing the system, or domain, into a number of discrete units typically referred to as finite elements. Once reduced, the domain can be represented by a system of equations that are solved, typically by computer, to predict the response of the domain to various external influences.

The invention is based in part on the discovery that when the level of contents within the drum is over about 80% full, gas within the head-space compresses and de-compresses as the drum lid moves in and out. The compressibility of the gas causes the resonant frequency of the lid to increase. This effect becomes even more pronounced as the volume of the head-space decreases (i.e., as the level of contents in the drum increases).

Surprisingly, however, the present inventors have also discovered that the compressibility of the gas does not affect the resonance of the higher modes. Thus, at these modes, the gas within the head-space does not compress and decompress as the drum vibrates. For this reason, the higher modes are less affected by the amount of head-space within the drum, or conversely, by the level to which the drum is filled.

Although other modes could be used, the second axisymmetric mode, which is easier to excite and identify, is preferred when measuring the frequency of the lid, which in turn is indicative of pressure. The fundamental mode, which radiates sound better than the other modes because it displaces the largest volume of air as the lid moves in and out, is preferred when measuring the frequency of the lid, which in turn is indicative of the volume of contents.

First, it was confirmed that the drum lid could be considered as independent of the entire drum assembly for the study of low frequency vibrations and that behavior of the other parts of the assembly could be ignored. In order to do so, an entire empty drum was modeled using FEM. The model revealed that the two lowest modes of vibration of the drum corresponded to the modes of vibration of the bottom and the lid, with no perceptible motion of the sides. Thus, it was concluded that vibration of the lid could be considered separate from the entire drum, especially when considering only the fundamental mode of the drum lid. This would be especially true of a filled drum since the contents of the drum would constrain any motion of the sides, or body, of the drum and dampen any vibrations.

The mode shapes of the drum lid were also determined using FE. Patel (1998). This aided in identifying which modes were being excited. One assumption made when modeling the drum lid vibration was that the lid was clamped at the edges. This means that the displacement and slope of the displacement (first derivative) with respect to the radius remained zero at the outer edges. Another assumption was that the pressure under the lid was uniform.

The actual shape of the drum lid was measured on the uninstalled lid across the diameter using a depth gauge. The thickness was measured using a micrometer across the diameter as well. These values were input to the model so that it would include the slight dome shape of the lid and, when appropriate, stiffening rings. The mode shapes predicted by the FE model were similar to those of a circular plate or membrane and can be found in several textbooks. Morse (1983); Reismann (1998). The results showed that resonance frequencies of the modes increased as the pressure within the drum increased. The FE results showed that the addition of a stiffening ring increased the resonance frequency of the fundamental mode and most of the other modes. The results also showed that the resonance frequency of all the modes increased as lid thickness increased. This effect was more pronounced for lids without stiffening rings.

Figure 1B:
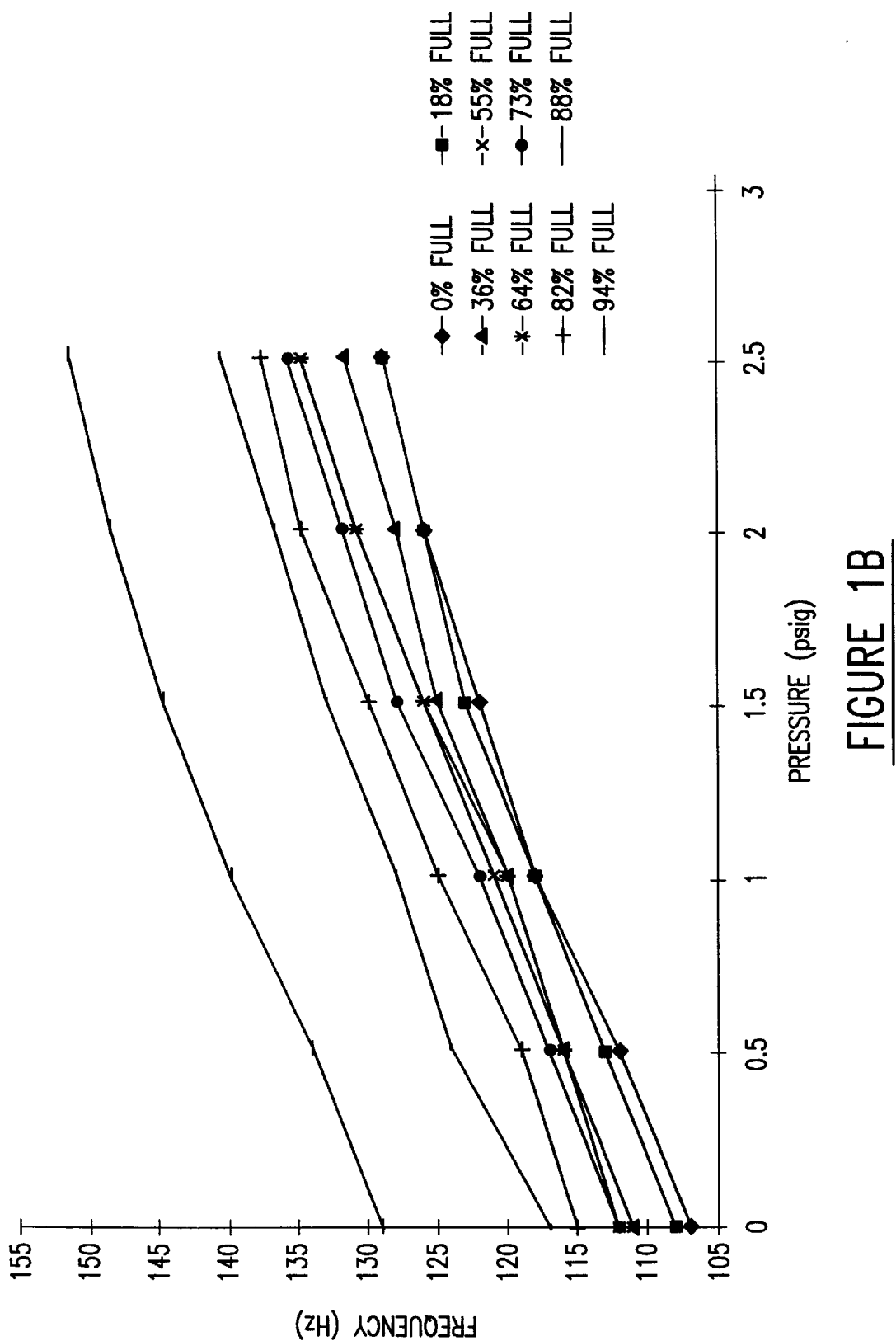
Figure 1C:
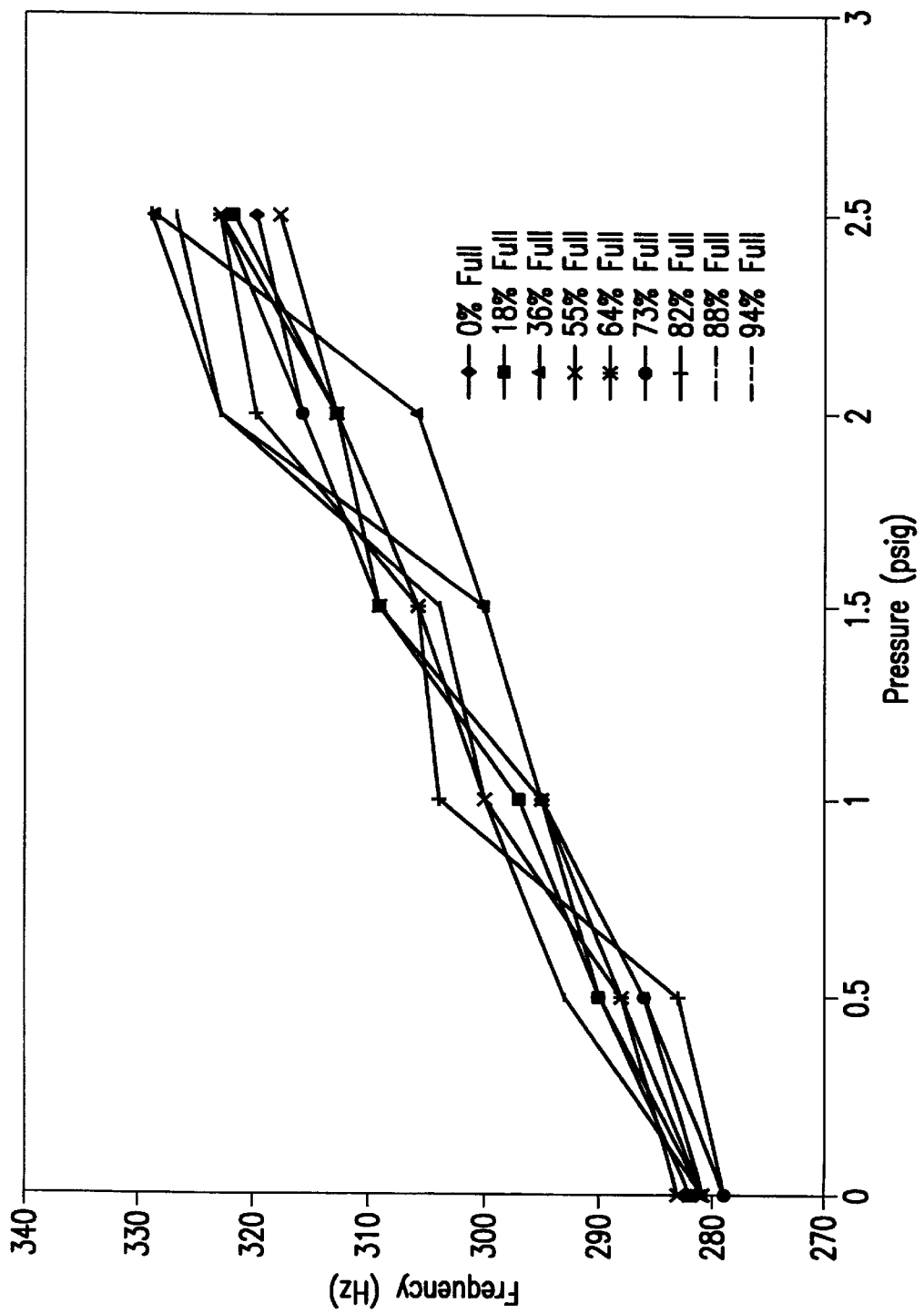

FIG. 1A shows how the frequency of the fundamental mode and the second axisymmetric mode vary with pressure and fill content. The different curves in the figure represent the drum filled with different levels of water. As seen in FIG. 1A, the frequency of the fundamental mode appears to increase as the level of contents increases. The level of contents in the drum affects the fundamental resonance frequency and not the resonant frequency of the second axisymmetric mode. As the lid vibrates in the fundamental mode, gas within the drum is alternately compressed and rarefied. This effect, found in kettledrums, is more pronounced as the volume of gas within the drum decreases and the level of contents in the drum increases. The second axisymmetric mode is not affected as much because the displacement of the drum lid, averaged over its total area, is very small. As a result, the drum volume does not change as the lid vibrates in this mode. Referring to FIG. 1B, frequency is plotted as a function of pressure within the drum for different fill levels. The legend gives the percentages of the drum that is filled with water. When the drum is 82% or more fill, the frequency is significantly higher than for lower fill levels. Referring to FIG. 1C, the second axisymmetric resonance is plotted for different fill levels. The scatter in the data in FIG. 1C shows that a given measurement is accurate within +/−10 Hz. FIG. 1C demonstrates that there is no clear relationship between frequency and fill level when using the second axisynimetric mode.

Thus, the second axisymmetric mode can be used to determine the frequency indicative of pressure (within 0.5 psi or so) and the fundamental mode can be used to determine the frequency indicative of fill level. In practice, the fundamental mode can be recorded with a microphone. If a high frequency is recorded, an accelerometer can then be used to measure the second axisymmetric mode to determine if the high frequency was due to pressure or level, or both. The second mode could be used instead of the second axisymmetric. In addition, it is possible to use other modes as well (e.g., third, fourth, . . . ).

The lid of a sealed container (or storage drum) is similar to the membrane of a musical drum. When a musical drum lid is tapped, it vibrates at specific frequencies that are determined by its diameter and the tension of the membrane. These specific frequencies correspond to the different modes of vibration of the drum lid. In accordance with the invention, two modes, preferably the fundamental mode and the second axisynimetric mode, are observed. As the pressure in the drum increases, the tension in the lid increases. As a result, the phase velocity of the flexural waves within the drum can be determined by measuring the frequency at which the drum lid resonates.

It can be seen that the dependence of frequency with fill level (depth of head-space) is much more pronounced for the fundamental mode than for the second axisymmetric mode. If the drum is relatively full, for example, the level of a 55-gallon drum is within four inches of the top, the resonant frequency of the fundamental mode will increase. However, this level has little or no effect on the resonant frequency of the second axisymmetric mode. Thus, the second axisymmetric mode is used to determine the frequency indicative of pressure. Once the pressure is determined, the fundamental mode can be used to determine the frequency indicative of the level of contents.

The resonant frequency of the drum lid is determined by exciting the lid so as to create at least two modes of vibration. This may be done, for example, by tapping on the lid with a soft object, such as a knuckle, an impact hammer with a soft tip, or a cymbal mallet. The resulting audible signal is then recorded using, for example, a microphone and/or an accelerometer. Standard signal processing techniques are used to convert the domain signals to frequency spectrum from which the resonant frequencies of the drum lid can be determined. These signal processing techniques can be performed with either software or hardware. The system can then be transported to several different platforms (i.e., palmtop computer, DSP based architecture, or other hardware).

Figure 3A:
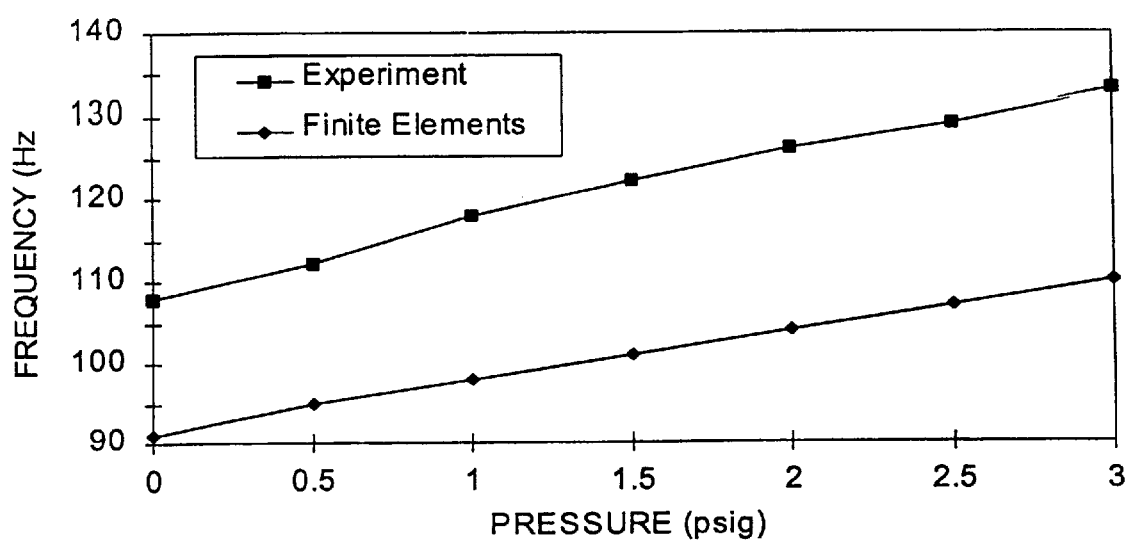
FIGS. 3A and 3B show the calculated and measured frequency responses of a drum lid as a function of internal drum pressure.
Figure 3B:
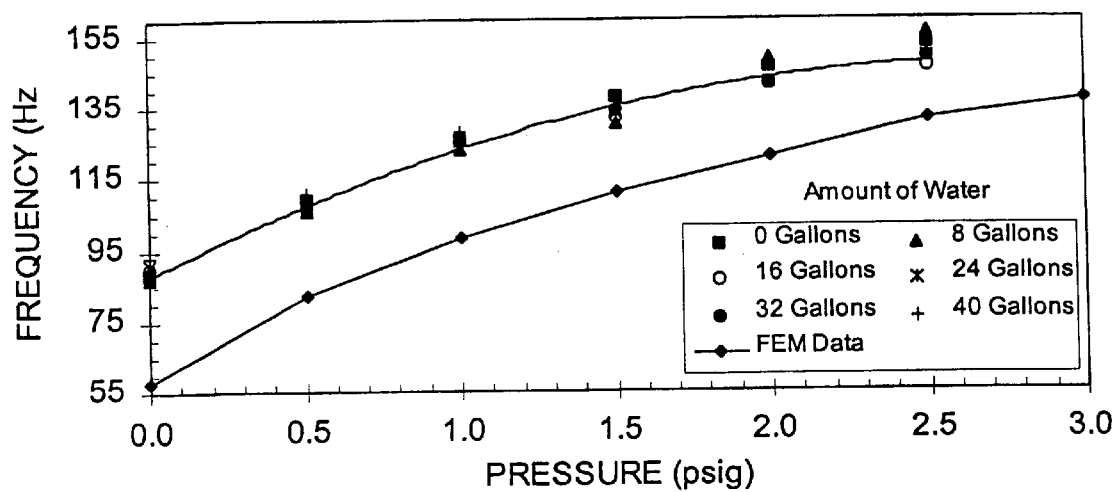
Figure 3C:
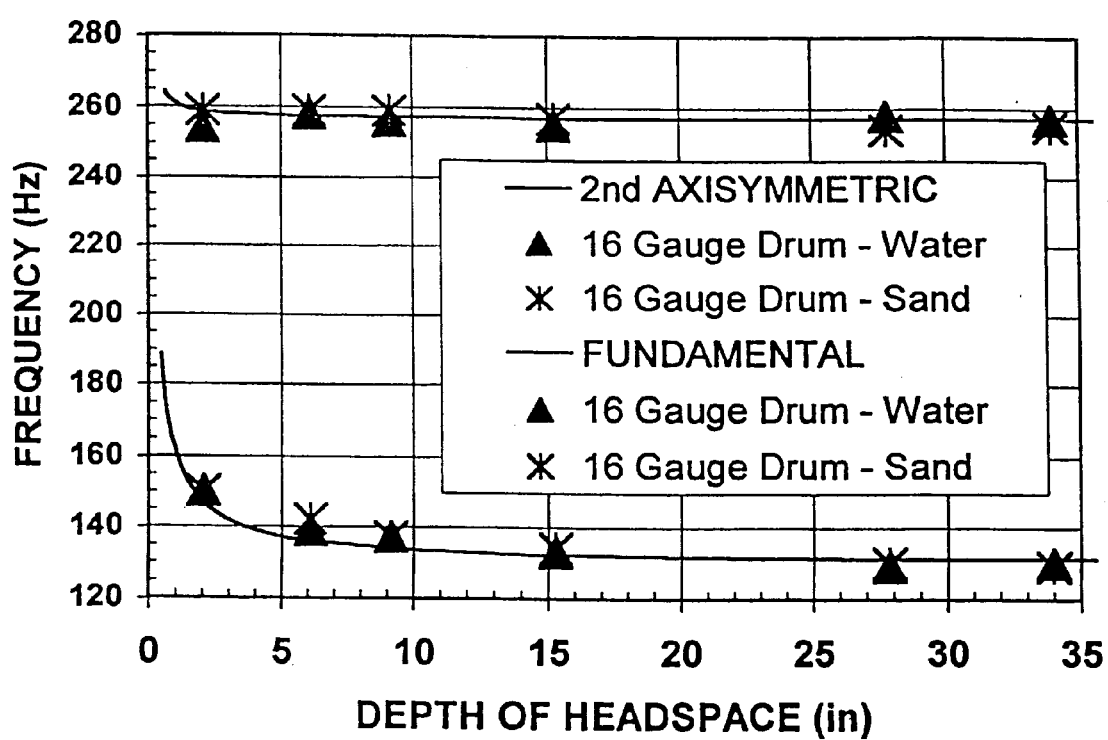
FIG. 3C shows the frequency response of the fundamental mode and the second axisymmetric mode as a function of fill level at 0 psig.

The head-space is the volume of gas above the level of contents. The calculated and measured frequency responses, of both the fundamental and the second axisymmetric mode, of a drum at ambient pressure (0 psi) are shown in FIGS. 3A and 3B. In FIG. 3A, the drum was 16 gauge steel (0.052 inch) and had a stiffening ring. In FIG. 3B, the drum was 18 gauge steel (0.047 inch) and did not have a stiffening ring.

Figure 2A:
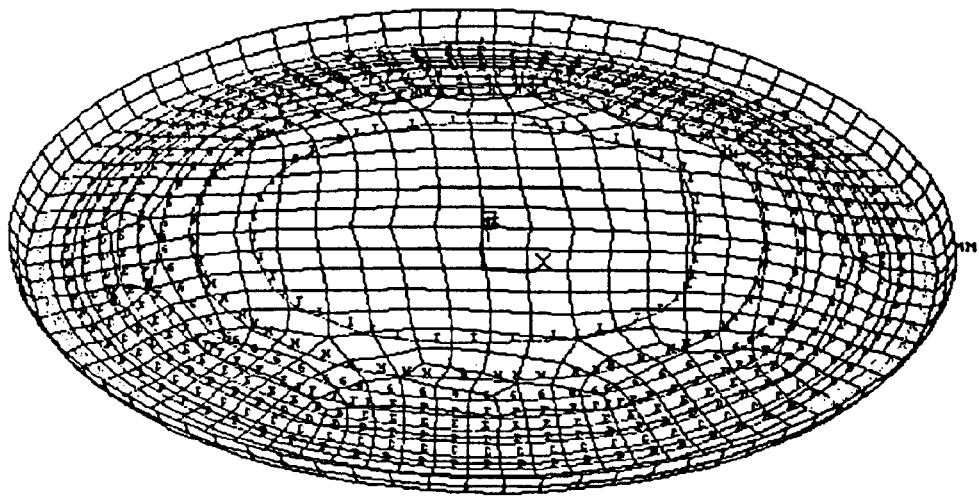
FIGS. 2A to 2C show computed mode shapes of the fundamental mode (FIG. 2A) and the second axisymmetric mode (FIGS. 2B and 2C) of a 55 gallon drum lid.
Figure 2B:
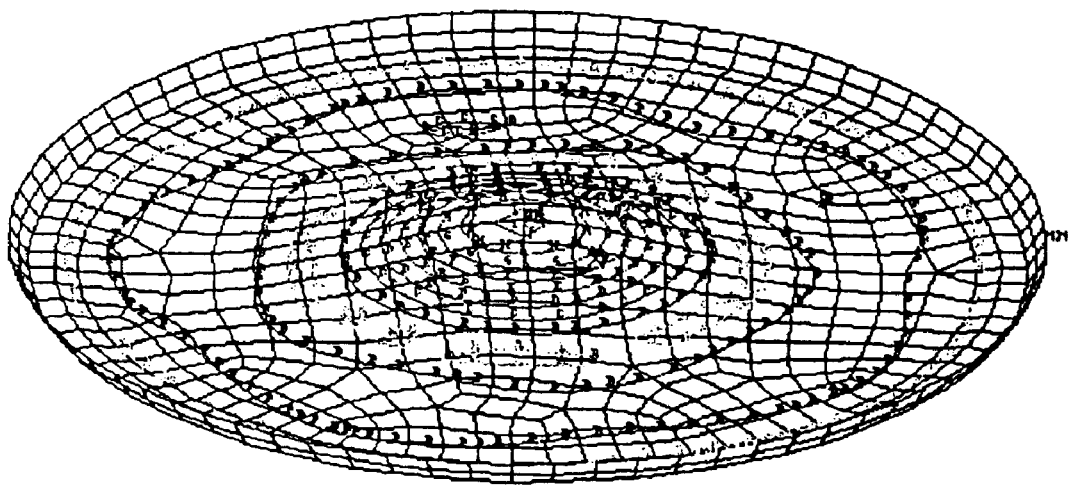
Figure 2C:
Figure 4A:
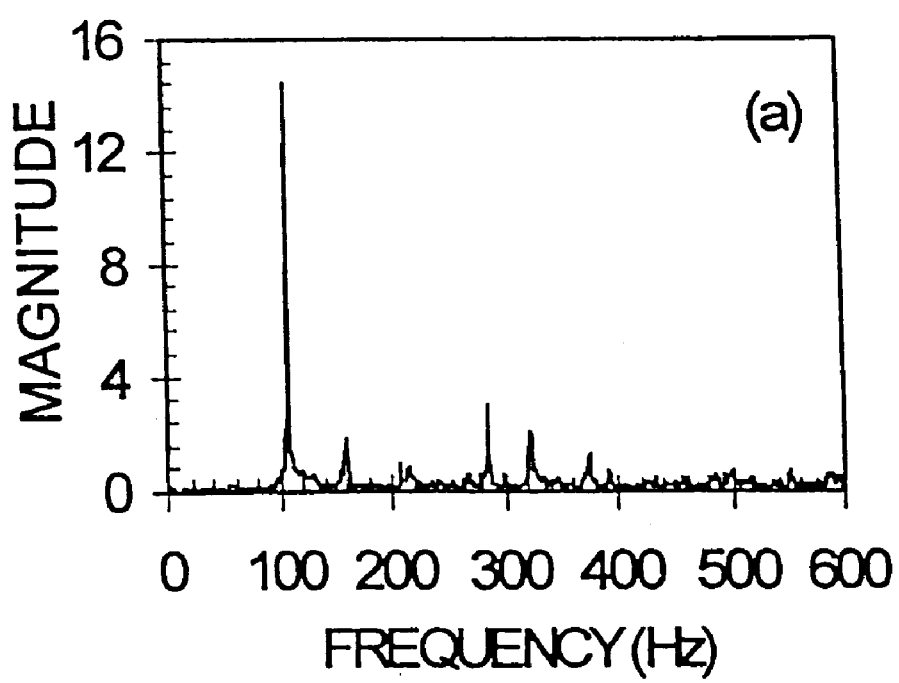
FIGS. 4A and 4B show frequency spectrums of a 55-gallon drum lid from microphone and accelerometer signals, respectively.
Figure 4B:
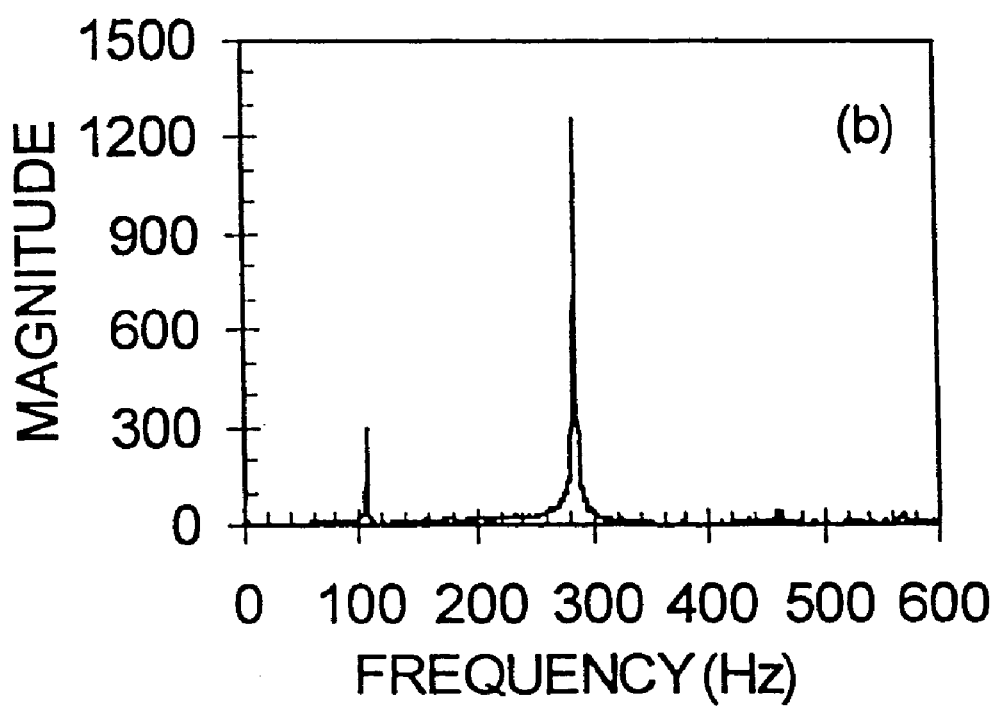

Frequency spectrums of a 55-gallon drum lid from microphone and accelerometer signals are shown in FIGS. 4A and 4B, respectively. The second axisymmetric mode cannot be detected easily with a microphone for the same reason that it is not affected by the level of contents in the drum, i.e., because this mode does not produce a net displacement of air, or gas. Computed mode shapes of the fundamental mode and the second axisymmetric mode of a 55 gallon drum lid are shown in FIGS. 2A–2C. As can be seen from FIGS. 2A–2C, as one part of the lid bulges out, another part bulges inward, so that there is no net displacement. Air (or gas) is not compressed or rarefied when this mode vibrates, it is just moved around.

EXAMPLE

As discussed above, a small change in the volume of the gas in the headspace of a container occurs as the lid vibrates up and down. This small change in volume causes a change in the internal pressure. The present inventors have discovered that this effect is significant for small head-space volumes, such as what occurs when the level of contents in the drum is high.

In order to investigate the effect of drum pressurization on lid vibration, several drums were configured so that they could be pressurized and so that the pressure could be measured independently of the technique being developed. Referring to FIG. 5E, the vibration of the drum lid (1) was detected by two means. An accelerometer (2), which was attached to the center of the lid (1), detected the vibration of the lid (1) directly. An microphone (3), which was mounted approximately 1 foot above the lid (1), detected the sound produced when the lid (1) was tapped. Therefore, the microphone (3) indirectly detected the vibration of the lid (1). An impact hammer (not shown) with a soft tip was used to strike the lid (1) and cause it to vibrate. The signals from the microphone (3) and accelerometer (2) were amplified in an amplifier (4) and low pass filtered in a filter (5) and then digitized on a digital oscilloscope (6). The cut off frequency of the filter was 2 kHz and the microphone and accelerometer data were digitized at 5 kHz. The impulse from the impact hammer was converted to frequency spectrum (7) and the frequency corresponding to the maximum signal was found (8). The data was then transferred to a microcomputer (9) where it was processed and analyzed.

Frequency spectra of the microphone and accelerometer signals from the same event (16 gauge steel drum lid (0.053 inch) with stiffening ring) are shown in FIGS. 4A and 4B. The signal was first recorded with a research grade microphone with bandwidth up to 20 kHz. The pressure within the drum was 0 psig when this signal was recorded. The prominent peak at approximately 100 Hz in FIG. 4A is due to the fundamental resonance of the drum lid. The signal from the accelerometer in FIG. 4B also contains a significant spike at 100 Hz that corresponds to the resonance of the fundamental. The prominent peak at approximately 280 Hz in FIG. 4B corresponds to the second axisymmetric mode of the lid.

The drum was pressurized to a given pressure, the drum was struck, and the signals from the microphone and the accelerometer were recorded. The frequency associated with the fundamental modes was determined by taking a Fast Fourier Transform of the signals. Data was taken at drum pressures from 0 to about 2.5 and later up to about 5.0 psig. Several different 55-gallon drum lids were investigated, including those with and without stiffening rings.

The following results were observed: (1) the resonant frequency of all of the modes, particularly the fundamental and the second axisymmetric mode, increased with pressure within the drum; (2) the presence of a stiffening ring affected the frequency response of the lid more than the lid thickness; (3) the dome height of the lid had little or no affect on frequency response; (4) the depth of the stiffening ring did affect the frequency response; (5) the level of contents within the drum affected frequency response of the fundamental, but not the second axisymmetric mode; (6) different contents affected the frequency response of the lid; (7) the damping coefficient associated with the first mode is different for different contents. Each of these results are discussed below.

The results from the FEM are compared with the experimental data for the microphone in FIG. 3A for a drum lid with a stiffening ring. The plot in FIG. 3B, which was obtained by microphone, is similar to FIG. 3A except that the drum lid did not have a stiffening ring. As can be seen in FIGS. 3A and 3B, the FE model roughly predicts the same change in frequency response with pressure (i.e., the same slope) that is observed in the data, except that the model prediction is approximately 20–30 Hz lower at each pressure.

The model did not take into account the following three factors: (1) the damping of the lid vibration; (2) the compressibility of the gas within the drum; and (3) the residual stresses introduced into the drum lid during the stamping process. The frequency calculated with FE would be reduced by adding damping to the model, thus moving the predicted values even farther from the experimental values. Therefore, this is probably not an important factor in this case. As discussed herein, the compressibility of the gas would increase the frequency calculated in the model. However, this is not an important factor when the head-space volume is 25% or greater than the total drum volume. Therefore, it is believed that the residual strains introduced in the stamping process probably cause the discrepancy between the FEM and the experimental results.

Comparison of FIGS. 3A and 3B show that the frequency response of the drum lid with the stiffening ring is higher than the response of the lid without the stiffening ring, as expected. A difference was predicted by the FE model, however it was not as large as the difference observed experimentally. FIG. 3B also shows the results of an experiment in which the drum was filled with different amounts of water. The frequency response of the drum was determined as a function of pressure for each fill level. There is no perceptible difference in response due to the different fill levels, up to 40 gallons (i,e., about 27% head-space).

Thus, the FE model accurately predicted the sensitivity that was observed experimentally in each of the two cases represented in FIGS. 3A and 3B. FE predicted 25 Hz/psi for the lid without the stiffening ring. The addition of the stiffening ring reduced the sensitivity to 6 Hz/psi.

Variation in Drum Lids

A major concern was whether the frequency response of a large population of drum lids would be similar. This is crucial if the technique is to be used to predict the pressure within a large population without having to calibrate each individual drum. To determine the variation in response, approximately 25 drum lids from the same manufacturer, but from 5 different lots, were tested on the same drum body. All but one of the lids were 18 gauge steel. The one exception was a lined 16 gauge drum lid. They were all of the same design and had stiffening rings. The resonant frequency of the fundamental mode is plotted as a function of drum pressure in FIG. 6A. The average responses at each pressure is plotted in FIG. 6B. The straight line is a linear least squares fit through these points. The error bars represent plus and minus 2 standard deviations of each of these averages.

Figure 6A:
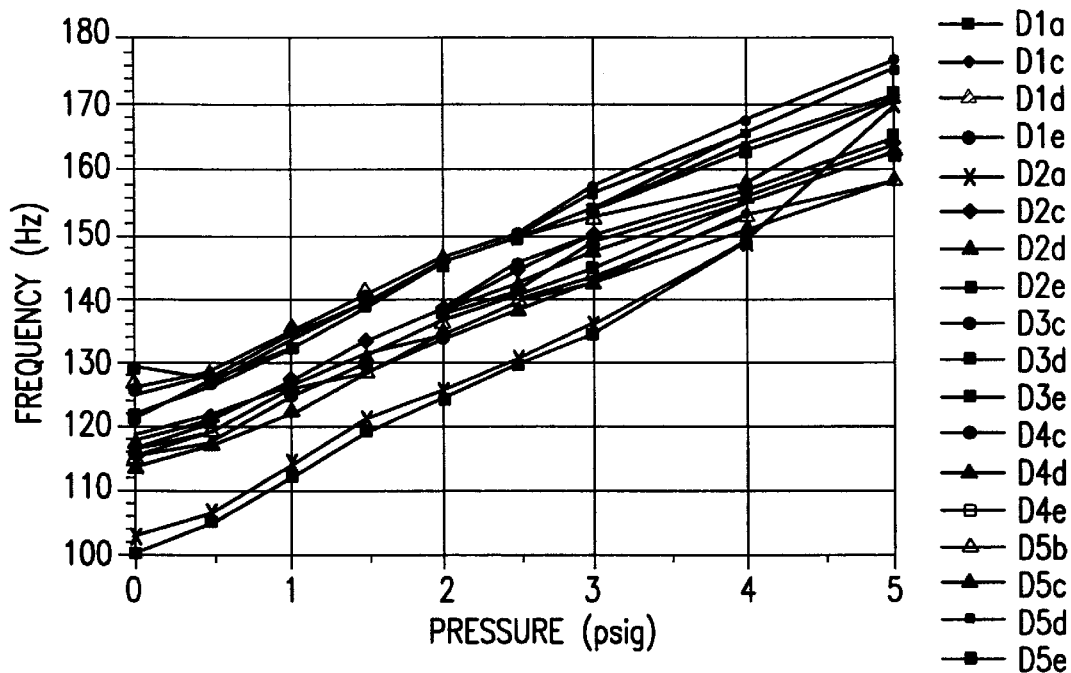
FIG. 6A is a graph showing the resonant frequency of the fundamental mode as a function of pressure.
Figure 7A:
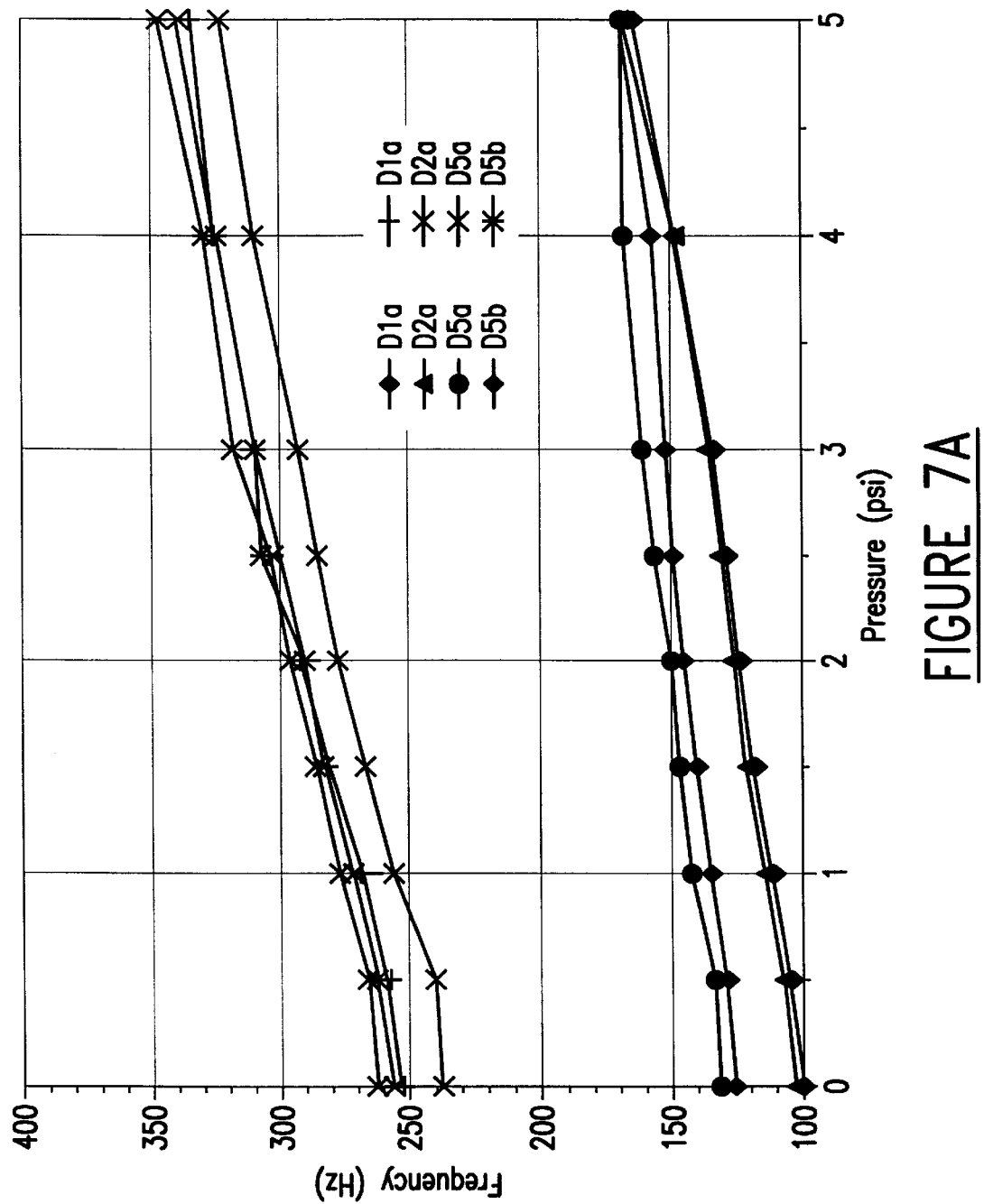
FIG. 7A is a graph showing the resonances of the fundamental and the second axisymmetric modes of the group of drum lids with the lower fundamental frequency from FIG. 6A.

The error bars indicate that the pressure within the drum can be predicted to within 1.2 psi. This level of precision is sufficient for most applications. However, this can be improved upon if needed. It can be seen in FIG. 6A that the response of 5 of the lids is considerably higher than the others. At 0 psig, the measured frequency is greater than 110 Hz. It turns out that the resonant frequency of the second axisymmetric mode enables these drum lids to be distinguished from the others. The resonances of the fundamental mode and the second axisymmetric mode of the group of drums with the lower fundamental frequency from FIG. 6A are plotted as a function of pressure in FIG. 7A. The same two resonances for the group of drum lids with the higher fundamental are plotted in FIG. 7B. FIG. 7A shows that both resonances increase with pressure. The second axisymmetric resonance increases from approximately 250 Hz at 0 psi to 325 Hz at 5 psi. For the group of drums in FIG. 7B, the second axisymmetric resonance is almost constant with pressure, at approximately 450 Hz. The characteristic that distinguishes these drums is the depth of the stiffening ring.

Figure 6B:
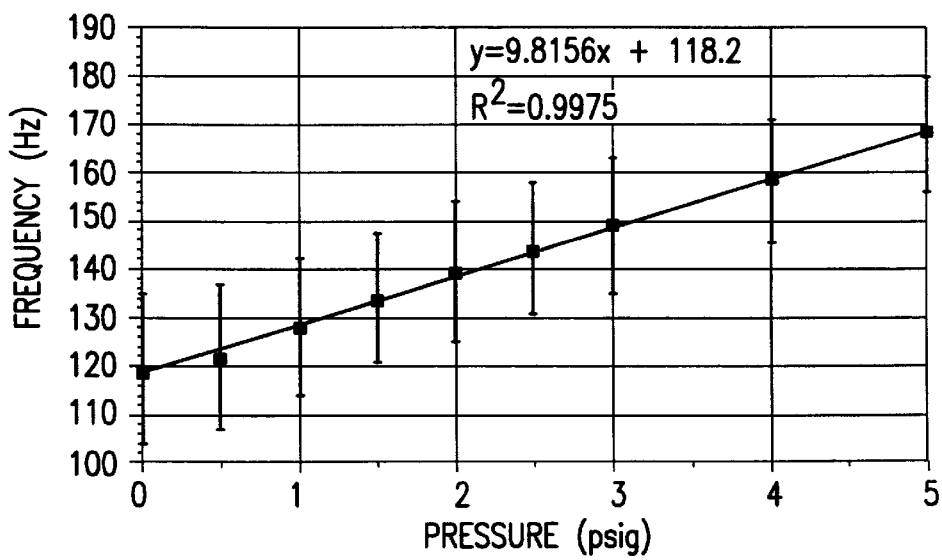
FIG. 6B shows the average responses at each pressure.

The depth of the stiffening ring of the drums in FIG. 7A is approximately 3 mm. The depth of the stiffening ring of the drums in FIG. 7B is approximately 5 mm. Thus, the frequency of the second axisymmetric mode could be used to distinguish between the two types of lids. The fundamental could then be used with more precision to predict the pressure within the drum. However, it is felt that the ±1.2 psi precision shown in FIG. 6B is suitable for most safety applications.

Figure 8:
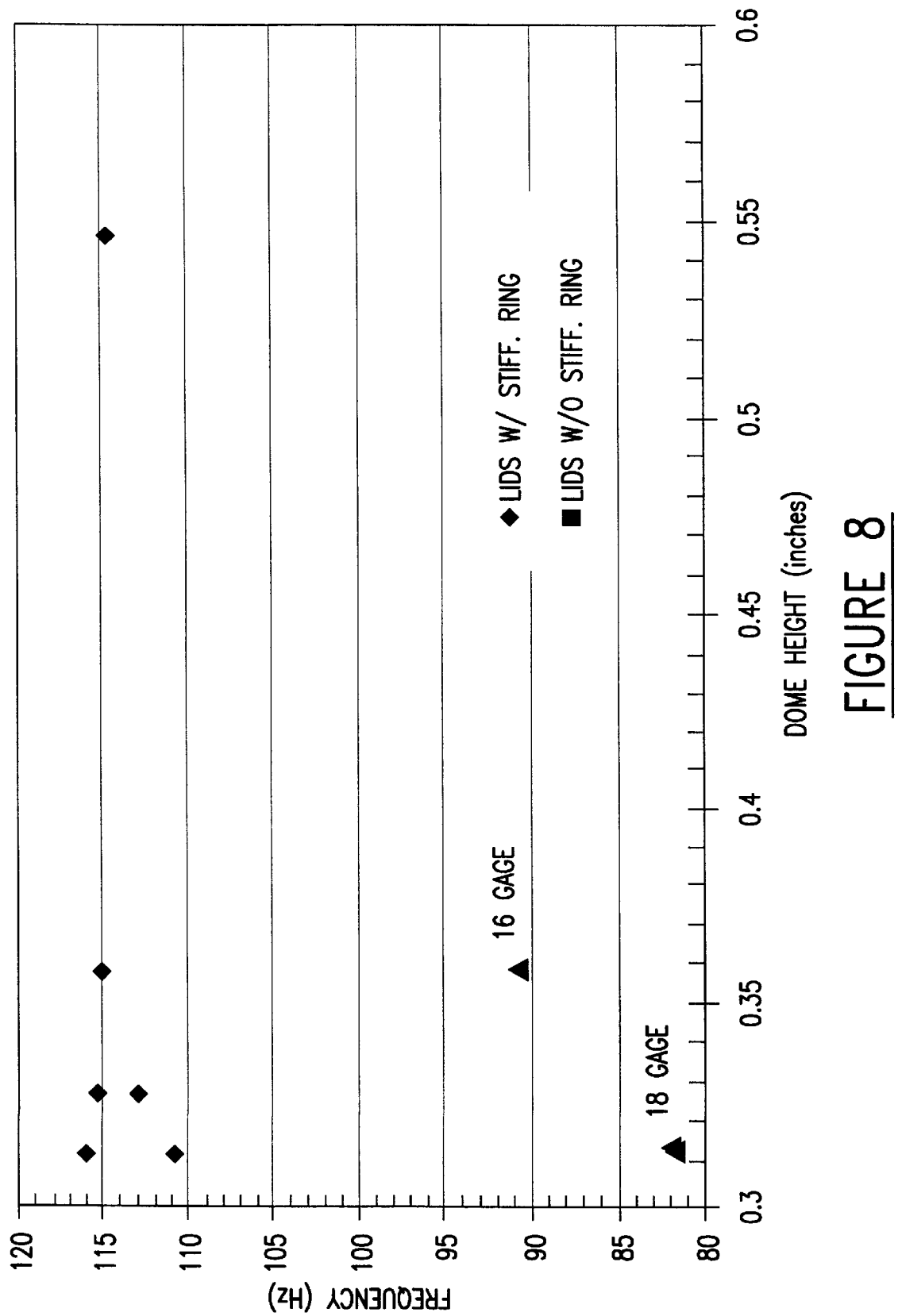
FIG. 8 is a graph showing the frequency response of the fundamental mode at 0 psi vs. dome height of the lid for several different drums.

It was also determined that the dome height of the lid had negligible affect on the frequency response of the lid. The frequency response of the fundamental at 0 psi is plotted versus dome height of the lid for several different drums in FIG. 8. The dome height changes by almost a factor of 2 for the drums with a stiffening ring. The resonant frequency for this group of drums differs by, at most, 5 Hz. And as noted in FIG. 7, the slope of the frequency response with pressure for these drums will be very similar. The responses of the drums without stiffening rings are significantly lower than the responses from the stiffening ring lids. Also, the response of the 16 gage lid (1.52 mm nominal thickness) is higher than the response of the 18 gage lid (1.21 nominal thickness), as predicted by FEM.

Thus, the lid thickness has a significant affect on the frequency response of non-stiffening ring drums. However, the thickness of the stiffening ring drums does not have a strong influence on their frequency response. The thickness of the drums in FIG. 6A ranges from 1.08 to 1.34 mm. Thus, the thickness of lids with stiffening rings affects the frequency response less that the lids without stiffening rings. Within the tolerances of this technique (say, ±1 psi), this parameter could possibly be ignored for the drums with stiffening rings.

Level of Contents

Figure 9:
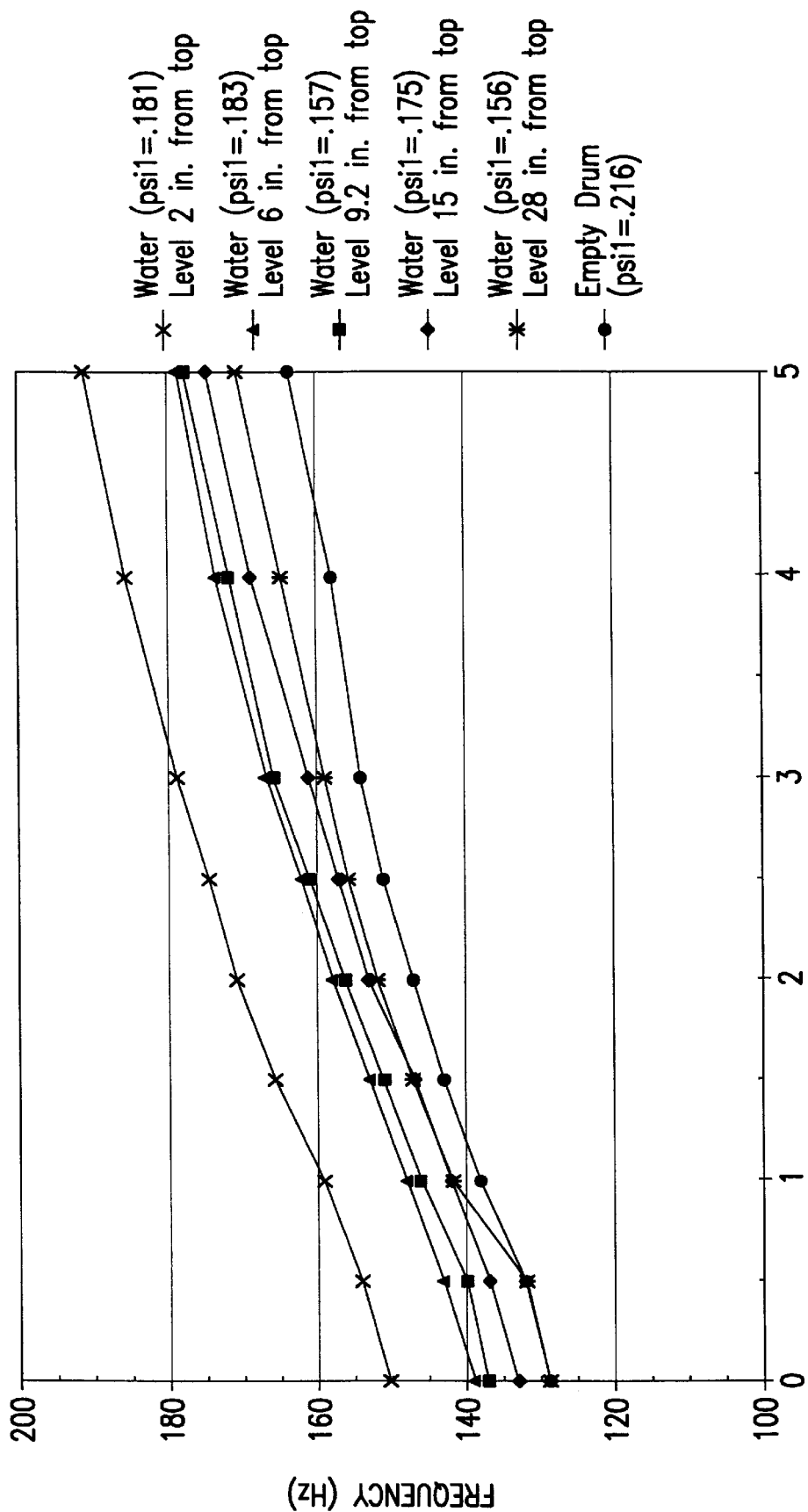
FIG. 9 is a graph showing the frequency response of the fundamental mode against drum pressure at various water levels.
Figure 10A:
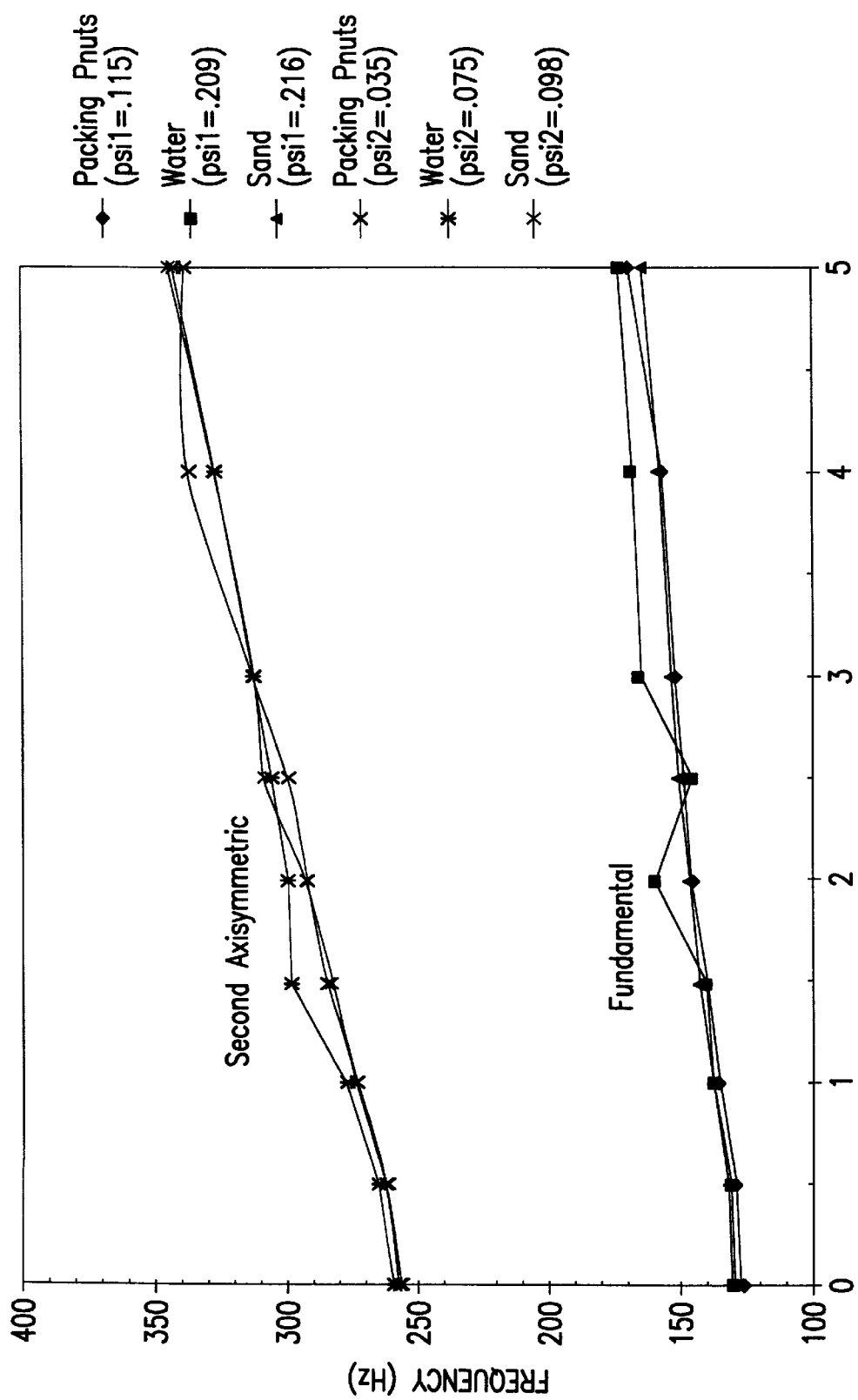
FIGS. 10A to 10F are graphs showing the frequency of the fundamental mode (lower set of lines) and the second axisymmetric mode (upper set of lines) as a function of drum pressure for different fill levels.
Figure 10B:
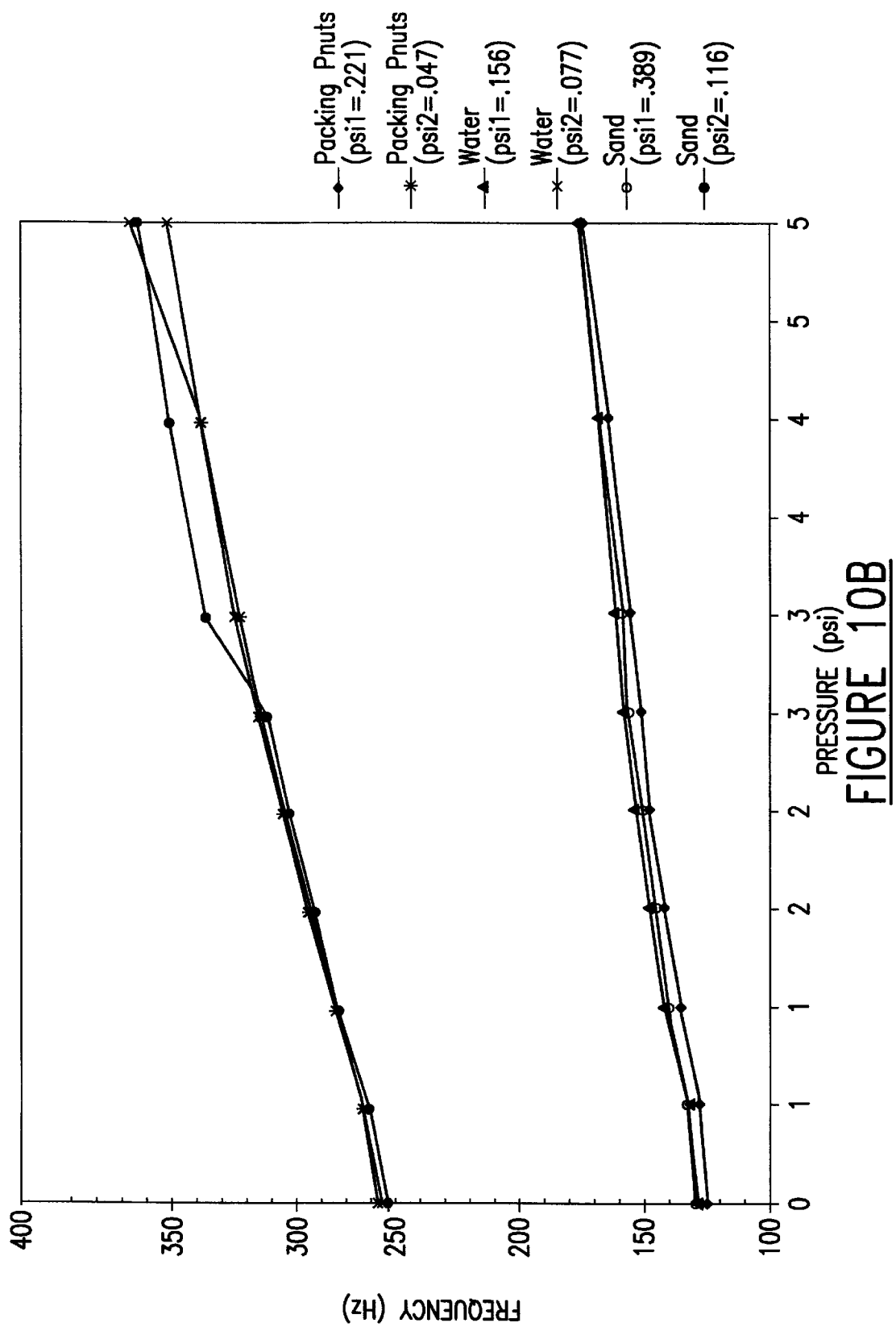
Figure 10C:
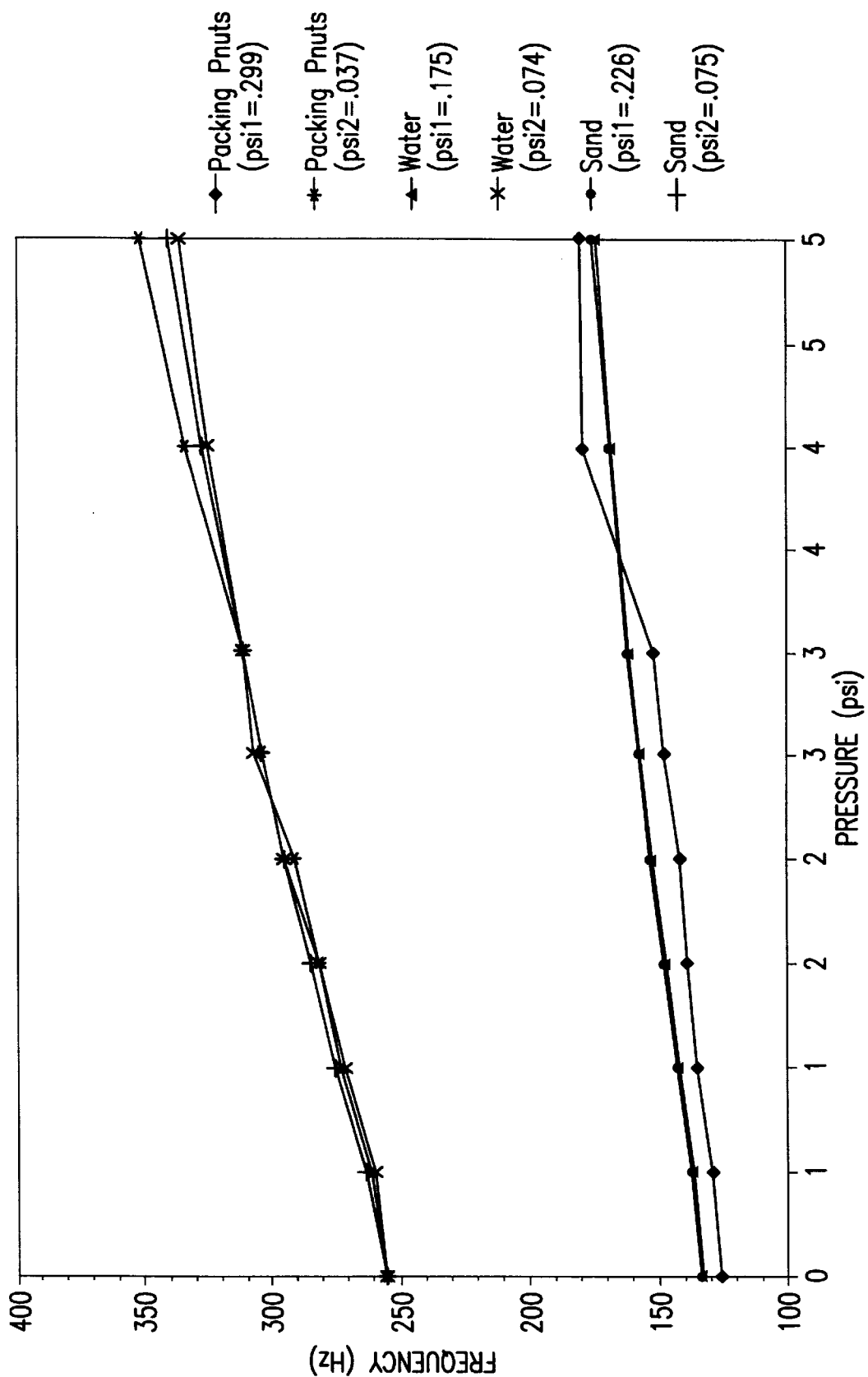
Figure 10D:
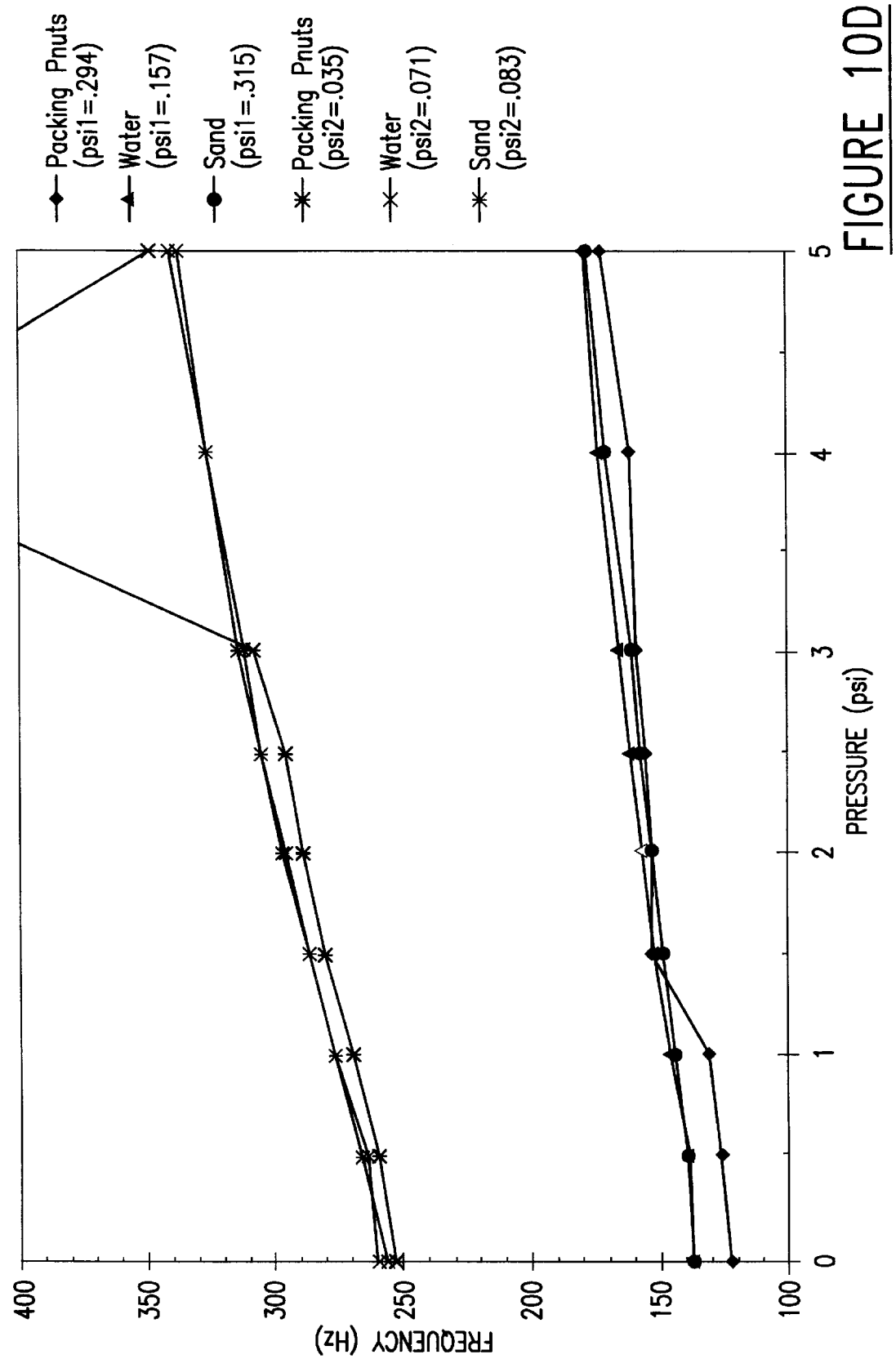
Figure 10E:
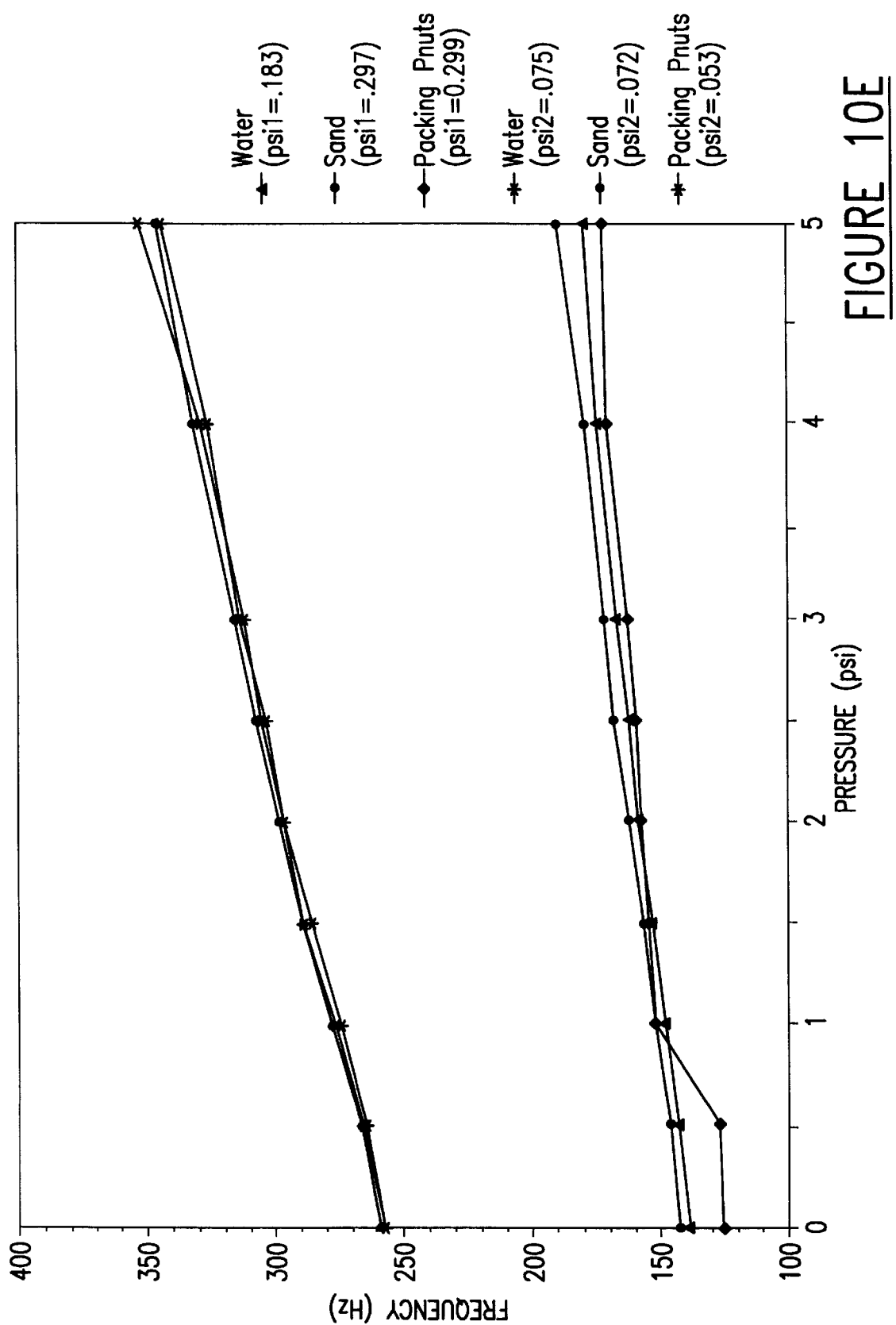
Figure 10F:
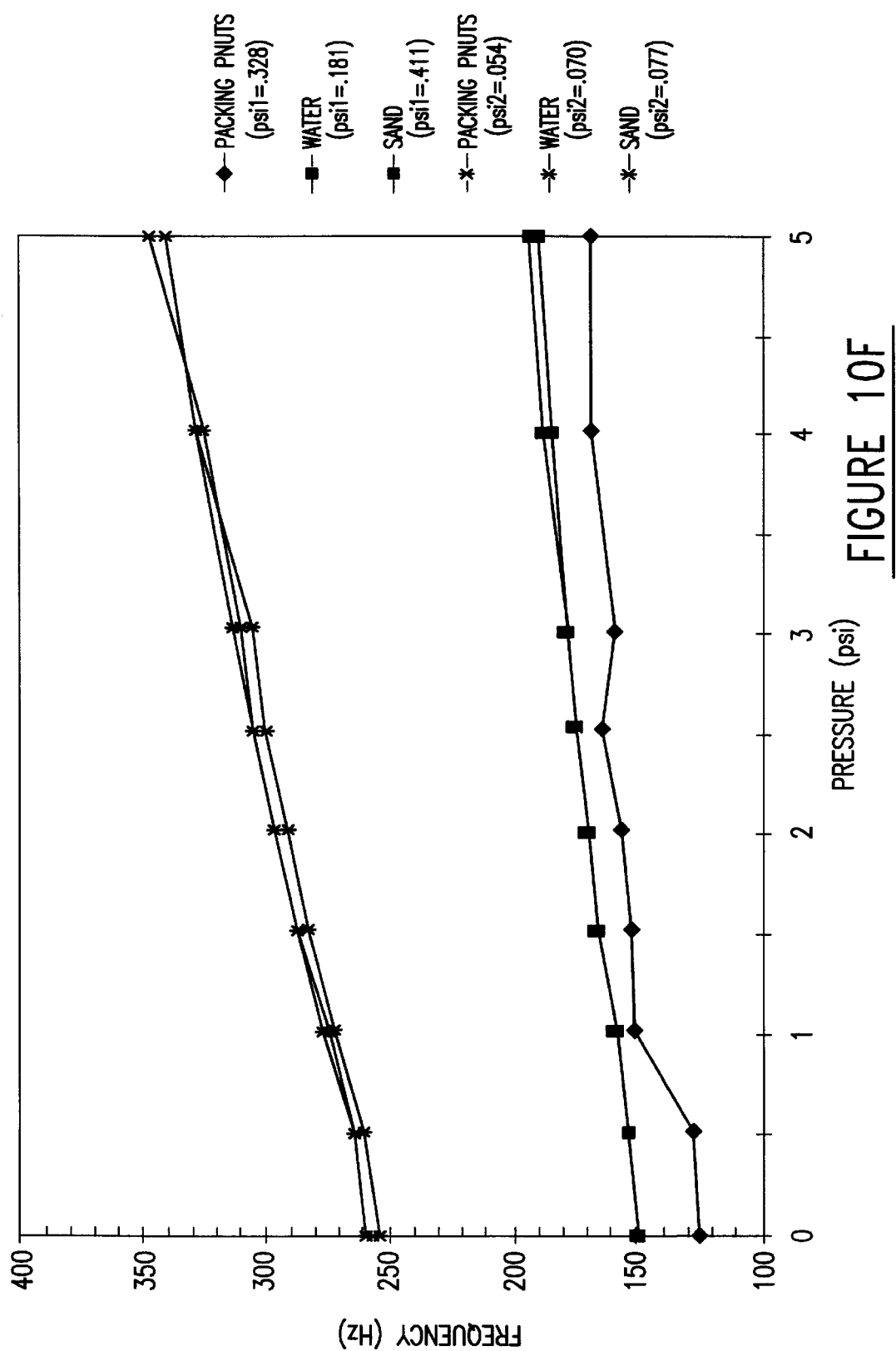

It was determined that the level of contents in the drum affects the fundamental resonant frequency of the lid when the volume of head-space is small. This can be seen in FIG. 9 in which the frequency of the fundamental is plotted against drum pressure. Each curve on the plot represents a different fill level of water in the drum, from 2 inches from the top to empty. As can be seen in FIG. 9, high fill levels cause the resonance frequency of the lid to increase. The effect is more pronounced at higher fill levels than at lower fill levels. The effect is caused by the compressibility of the head-space gas, which in this case is air. As the lid vibrates up and down, the volume of the head-space increases and decreases. Decreasing the volume of the headspace will cause the internal pressure to increase, and vice versa. The change in pressure becomes more pronounced as the volume of head-space decreases since the change in volume due to the vibrating lid becomes a larger percentage of the total volume.

However, the level of contents in the drum does not affect the resonance of the second axisymmetric mode. The reason is that this mode does not change the head-space volume. Compare the fundamental and second axisymmetric mode shapes, which are plotted in FIGS. 2A to 2C. As mentioned earlier, the shape of the lid has a slight dome shape when at rest. In the fundamental mode, the lid vibrates in and out from this equilibrium position. The net change in volume can be determined by calculating the average, maximum displacement of the lid. In the second axisymmetric mode, as the center part of the lid displaces outward, the outer area of the lid displaces inward so that the average displacement over the entire lid surface is negligible. As a result, this mode does not compress the head-space gas.

This can be seen from the results plotted in FIGS. 10A–F. The frequency of the fundamental mode and the second axisymmetric mode are plotted as a function of drum pressure for different fill levels. The fill levels were measured from the top of the drum and range from empty (34 inches) to almost full (2 inches). The drums were filled with sand, water, and Styrofoar™ packing peanuts. The second mode resonance, which starts at approximately 250 Hz at 0 psi, is not affected by fill level.

Under this scenario, the frequency of the fundamental would first be determined by measurements with a microphone. If the frequency reading indicated that the drum might be pressurized, then the frequency of the second axisymmetric mode would be determined with an accelerometer. This information would let the inspector determine whether the first reading was high due to pressure or level. However, if the drum lid had a deep stiffening ring, such as those represented in FIG. 7B, the second mode would not allow the inspector to make this determination.

Fortunately, the effect of a high level of contents or a deep stiffening ring cause the frequency of the fundamental to increase, thus causing a false positive reading. In other words, either of these situations would cause an inspector to determine that the pressure within the drum was elevated when it might not be. These situations, while inconvenient, increase the safety of those handling the drums.

Damping

Figure 11:
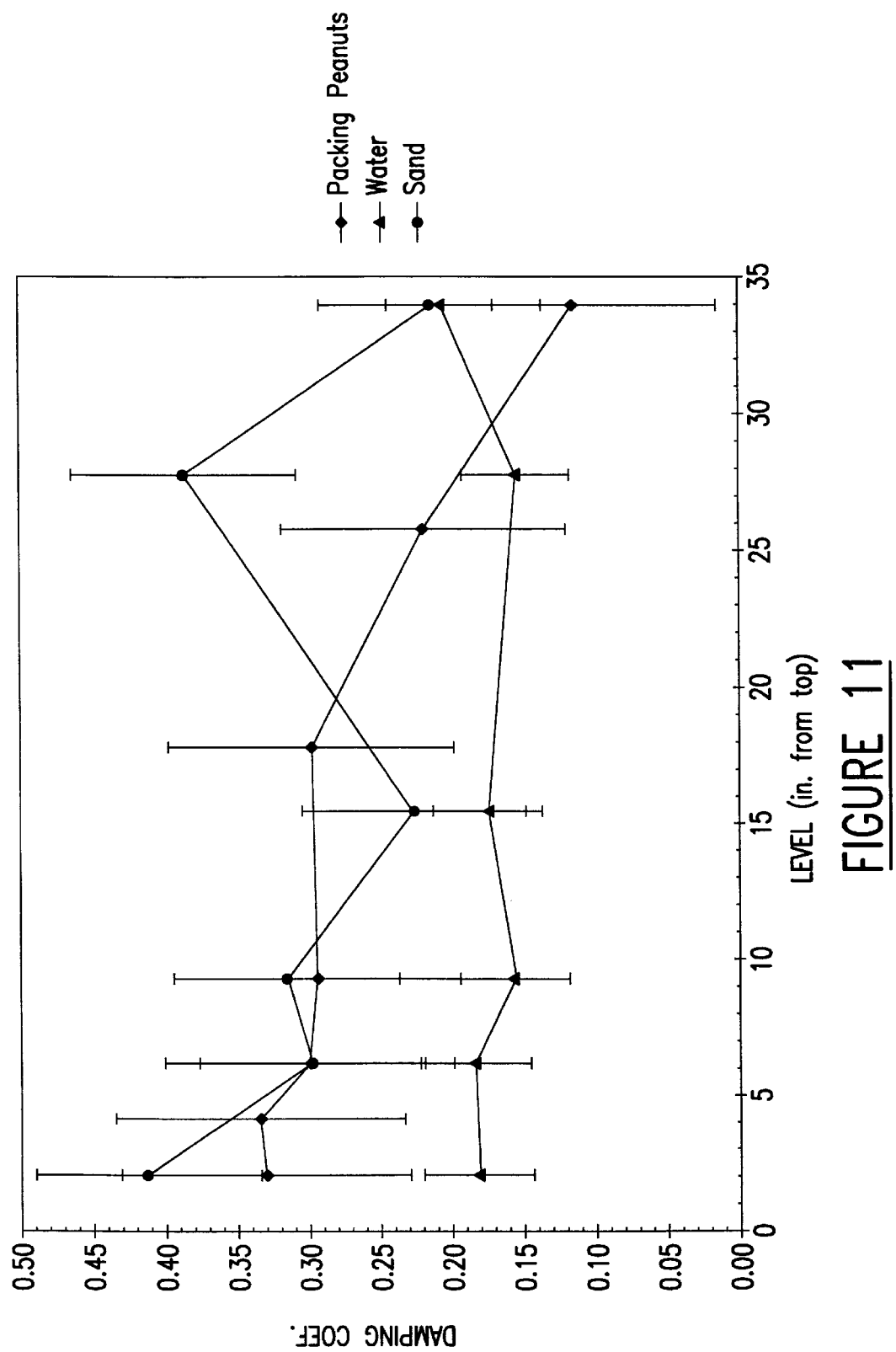
FIG. 11 is a graph showing the damping coefficient ψ associated with the fundamental mode for a drum filled with different levels of water, sand and Styrofoam™ packing peanuts.

The damping of the fundamental mode and the second axisymmetric mode was determined. A convenient method for doing this is to measure the width of the frequency peaks shown in FIGS. 4A and 4B. A broad peak indicates higher damping than a narrow one. The damping coefficient, $\Psi$, associated with the fundamental mode for a drum filled to different levels with water, sand and packing peanuts is plotted in FIG. 11. The data used for this plot is the same as that used in FIGS. 10A to 10F. The damping coefficient plotted is averaged over all of the pressure data, from 0 to 5 psig. The error bars represent the standard deviations calculated from these averages. The damping coefficient did not appear to be a function of internal pressure, within experimental error.

The plot indicates that, at the higher fill levels, the damping is higher in the drums containing sand and packing peanuts than with water. This difference could be due to differences in porosity, acoustic impedance, or bulk modulus of the materials.

As opposed to the damping coefficient of the first mode, no correlation between the damping coefficient of the second axisymmetric mode and fill level, contents, or pressure was observed.

The present inventors have shown that the frequency of vibration of the lid on a 55 gallon drum is proportional to the pressure inside the drum. The present inventors have also shown that the response of the drum lid is altered when the drum is over 80% full.

According to another embodiment, the invention includes an instrument that can be used to test drums for pressure and volume of contents in the field. This instrument can be hand held, utilizing a microphone which has certain advantages over an accelerometer. The most important of these is that by using a microphone an inspector would save time since contact with the drum would be minimized. The inspector would simply tap the drum, the signal would be recorded with a microphone that was either internal to the device or attached to a lapel, the signal would be recorded, and the inspector would move on to the next drum. Another advantage is that the spectrum from the microphone signal is usually much simpler, since many of the higher modes do not radiate acoustically. Thus, the spectrum is easier to interpret with software.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

REFERENCES

1. Patel, H., et al., Drum Pressure Monitor, Review of Progress in Quantitative Nondestructive Evaluation, Vol. 18 (1999).
2. Patel, H., The Mode Shapes and Natural Frequencies of Various Types of Storage Drums Under Different Pressures, Master's Thesis, Mississippi State University (1998).
3. Morse, P. M., Vibration and Sound American Institute of Physics, Chapter 5, Sections 19 and 21 (1983).
4. Reismann, H., Elastic Plates Theory and Application, Chapters 6 and 7 (1988).
5. Thinnes, G. L., et al., Resonance Analysis to Determine Pressurization of 55 Gallon Waste Containers, Idaho National Engineering Laboratory Report, INEL-95/0635 (1995) (unpublished).

What is claimed is:

1. A method for determining an internal pressure of a sealed container, comprising:

exciting a lid of the sealed container so as to create at least two modes of vibration having separate frequencies, wherein said frequencies are fundamental, $f_1$, and a second frequency, $f_2$;

detecting the vibration resulting from said exciting to determine $f_1$, and $f_2$;

using $f_2$, which is indicative of internal pressure, to calculate a first value for internal pressure using a first mathematical model that is calibrated to the lid on the sealed container;

using $f_1$, which is indicative of volume of contents, to calculate the volume of contents in the sealed container using a second mathematical model that is calibrated to the lid on the sealed container;

wherein a natural frequency of said lid is a function of internal pressure and volume of contents; and compensating for said volume of contents to determine a second value for internal pressure, wherein said second value for internal pressure is more reliable than said first value for internal pressure.

2. The method of claim 1, wherein $f_2$ is the second axisymmetric mode.

3. An apparatus for determining an internal pressure of a sealed container, comprising:

means for exciting a lid of the sealed container so as to create at least two modes of vibration having separate frequencies, wherein said frequencies are fundamental, $fd_1$; and a second frequency, $f_2$;

detecting means for detecting vibration resulting from the exciting of said container to determine $f_1$ and $f_2$;

calculating means for calculating a first value for internal pressure of said container using $f_2$;

calculating means for calculating the volume of contents of said container using $f_1$;

wherein a natural frequency of said lid is a function of said internal pressure and said volume of contents; and calculating means for compensating for said volume of contents to determine a second value for internal pressure, wherein said second value for internal pressure is more reliable than said first value for internal pressure.

4. The method of claim 3, wherein $f_2$ is the second axisymmetric mode.

5. A method of determining the internal pressure and level of contents within a container comprising the steps of:

(a) storing container data into a memory;

(b) exciting a lid of the container so as to create at least two modes of vibration having separate frequencies, wherein said frequencies are fundamental, $f_1$, and a second frequency, $f_2$;

(c) detecting the vibration resulting from said exciting to determine $f_1$ and $f_2$;

(d) producing a frequency spectrum of the detected vibration;

(e) isolating values of $f_1$ and $f_2$ from the frequency spectrum;

(f) using $f_2$ to calculate an internal pressure using a first mathematical model that is calibrated to the sealed container; and (g) using $f_1$ to calculate the volume of contents in the sealed container using a second mathematical model that is calibrated to the sealed container.

6. The method of claim 5, wherein $f_2$ is the second axisymmetric mode.

* * * * *

UNITED STATES PATENT AND TRADEMARK OFFICE
CERTIFICATE OF CORRECTION

PATENT NO. : 6,339,960 B1  Page 1 of 1
DATED : January 22, 2002
INVENTOR(S) : R. Daniel Costley et al.

It is certified that error appears in the above-identified patent and that said Letters Patent is hereby corrected as shown below:

<u>Title page,</u>
Item [56], References Cited, please insert the following:
-- This invention was made with U.S. Government support under contract number DE-FG02-93CH10575 awarded by the Department of Energy. The U.S. Government may have certain rights in this invention. --

<u>Column 7,</u>
Line 8, "An microphone" should read -- A microphone --.

<u>Column 12,</u>
Line 8, "$fd_1$" should read -- $f_1$ --.

Figure 5A:
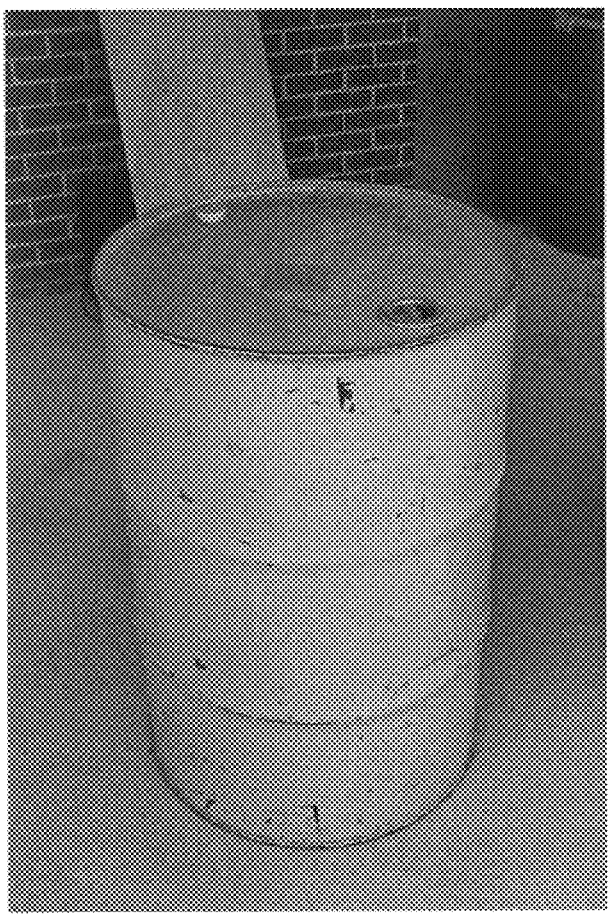
FIGS. 5A and 5B show a tight-head drum.
Figure 5B:
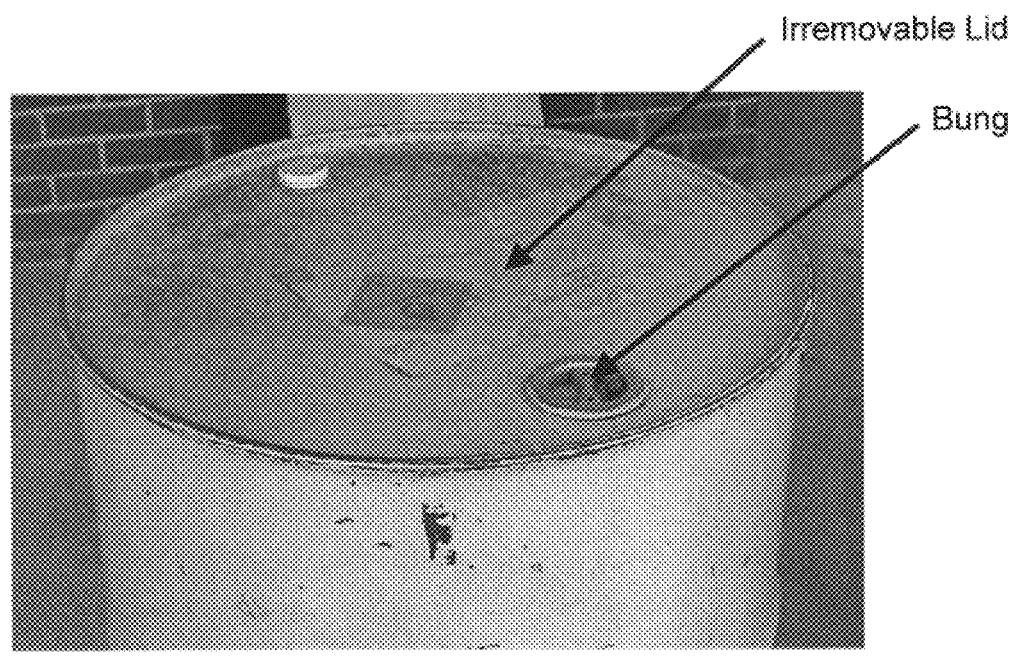
Figure 5C:
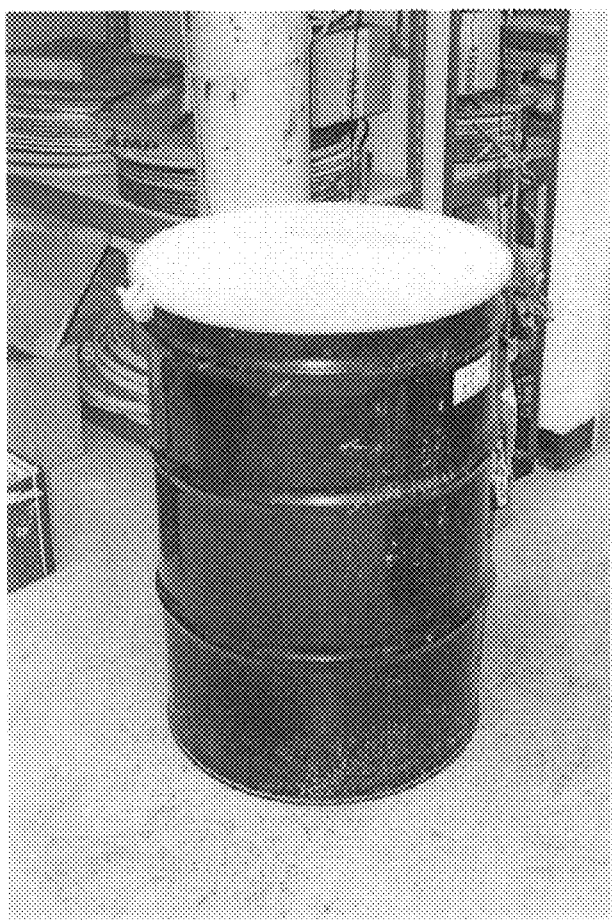
FIGS. 5C and 5D show a open-head drum.
Figure 5D:
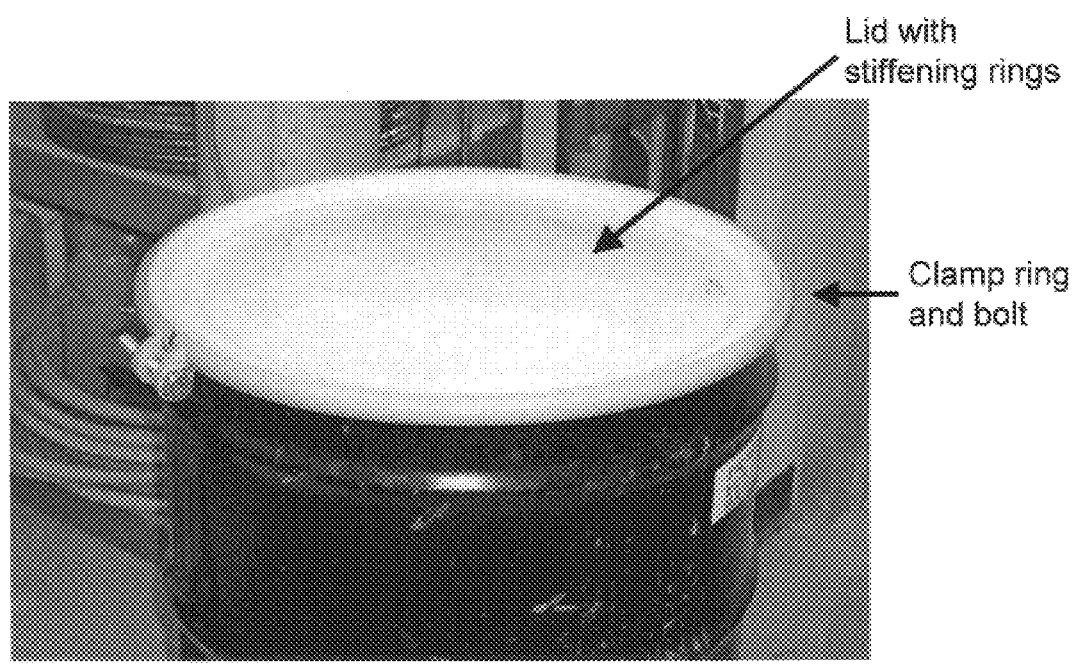
Figure 5E:
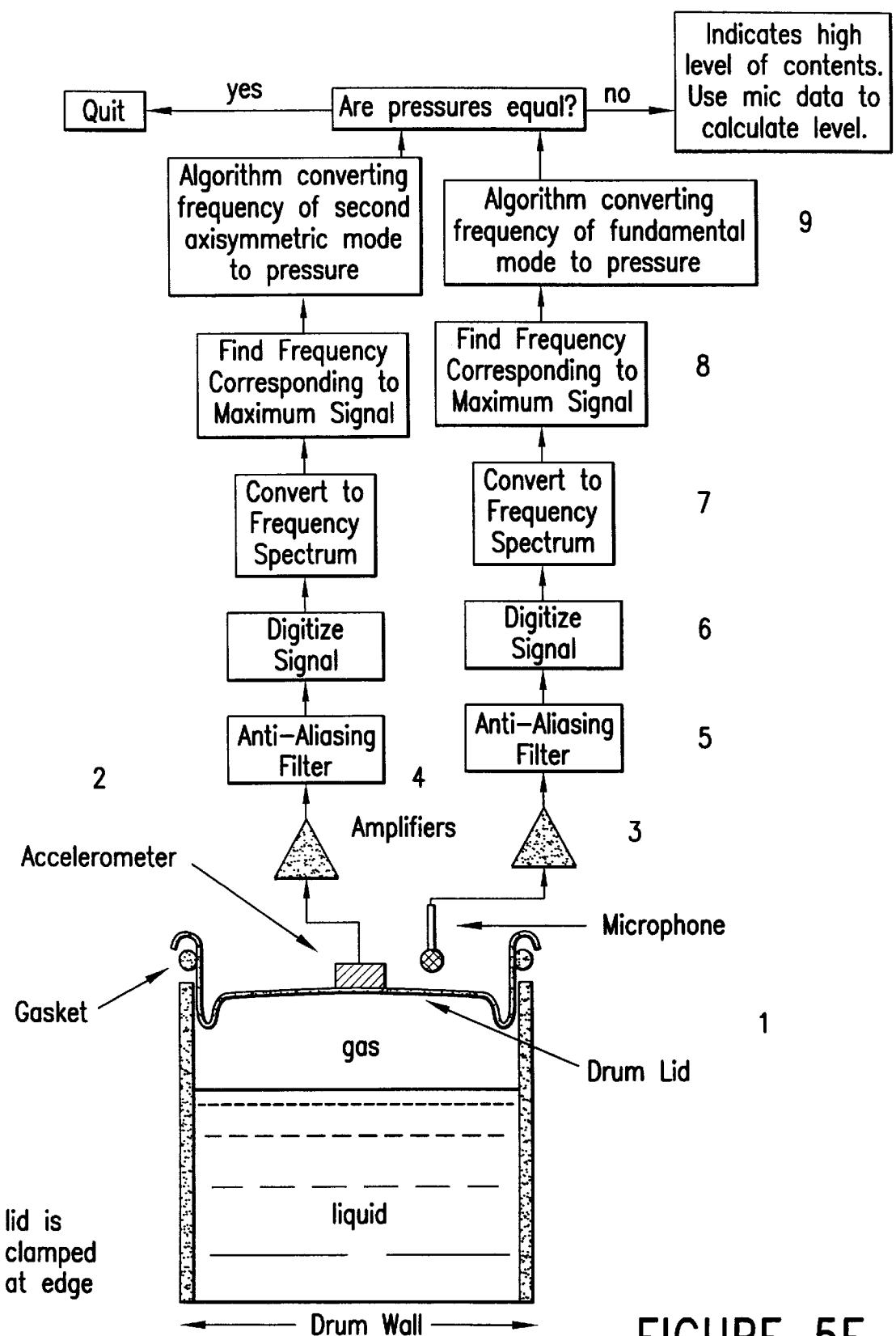
FIG. 5E shows the apparatus of the invention being used.

<u>Drawings,</u>
Figure 5D, lines 1-2, (Sheet 13 of 26), "Lid with stiffening rings" should read -- Lid with stiffening ring --.

Signed and Sealed this

Twenty-fifth Day of June, 2002

Attest:

Attesting Officer

JAMES E. ROGAN
*Director of the United States Patent and Trademark Office*